US012807983B2

(12) United States Patent
Sim et al.

(10) Patent No.: US 12,807,983 B2
(45) Date of Patent: *Nov. 24, 2026

(54) METHOD FOR SYNTHESIZING SINGLE METAL NANOBRIDGED STRUCTURE AND METHOD FOR MANUFACTURING DNA POINT MUTATION DETECTION SENSOR BY USING SAME

(71) Applicant: Korea University Research and Business Foundation, Seoul (KR)

(72) Inventors: Sang Jun Sim, Seoul (KR); Xingyi Ma, Jinan (CN); Soohyun Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 1177 days.

This patent is subject to a terminal disclaimer.

(21) Appl. No.: 17/266,193

(22) PCT Filed: Aug. 14, 2019

(86) PCT No.: PCT/KR2019/010370

§ 371 (c)(1),
(2) Date: Feb. 5, 2021

(87) PCT Pub. No.: WO2020/036438

PCT Pub. Date: Feb. 20, 2020

(65) Prior Publication Data

US 2022/0364162 A1 Nov. 17, 2022

(30) Foreign Application Priority Data

Aug. 14, 2018 (KR) ........................ 10-2018-0095140
Aug. 14, 2019 (KR) ........................ 10-2019-0099454

(51) Int. Cl.
*C12Q 1/6825* (2018.01)
*B82Y 5/00* (2011.01)
*B82Y 15/00* (2011.01)
*B82Y 40/00* (2011.01)
*C12Q 1/6827* (2018.01)

(52) U.S. Cl.
CPC ............ *C12Q 1/6825* (2013.01); *B82Y 15/00* (2013.01); *C12Q 1/6827* (2013.01); *B82Y 5/00* (2013.01); *B82Y 40/00* (2013.01)

(58) Field of Classification Search
None
See application file for complete search history.

(56) References Cited

U.S. PATENT DOCUMENTS 8,012,743 B2 9/2011 Bamdad et al.
8,105,780 B2 1/2012 Su et al.
2004/0235016 A1* 11/2004 Hamers .................. B82Y 30/00 435/6.19
2012/0107242 A1* 5/2012 Wang ....................... A61K 9/51 424/9.1
2013/0029360 A1 1/2013 Suh et al.

FOREIGN PATENT DOCUMENTS

CN 102811943 A 12/2012
EP 2 511 231 A2 10/2012
JP 2008-524602 A 7/2008
KR 10-2011-0066881 A 6/2011
KR 10-2012-0056024 A 6/2012
KR 10-2014-0141880 A 12/2014
KR 10-1484743 B1 1/2015
WO WO-03054931 A1 * 7/2003 ............. B82Y 15/00
WO WO 2004/096986 A2 11/2004
WO WO2014149071 A1 * 9/2014 ............... C12Q 1/68
WO WO2015023059 * 2/2015

OTHER PUBLICATIONS

Ma X, et al. Single gold nanoplasmonic sensor for clinical cancer diagnosis based on specific interaction between nucleic acids and protein. Biosens Bioelectron. May 15, 2015;67:59-65. Epub Jun. 24, 2014. (Year: 2014).*
Martinsson E, et al. Optimizing the refractive index sensitivity of plasmonically coupled gold nanoparticles. Plasmonics. Dec. 24, 2013;9(4):773-80. (Year: 2013).*
Abdul Rasheed P, Sandhyarani N. Attomolar detection of BRCA1 gene based on gold nanoparticle assisted signal amplification. Biosens Bioelectron. Mar. 15, 2015;65:333-40. Epub Oct. 30, 2014. (Year: 2014).*
Weizmann Y, et al. Telomerase-generated templates for the growing of metal nanowires. Nano Letters. Apr. 3, 2004;4(5):787-92 (Year: 2004).*
Brown KR, Natan MJ. Hydroxylamine seeding of colloidal au nanoparticles in solution and on surfaces. Langmuir. Jan. 22, 1998;14(4):726-8 (Year: 1998).*
How thiol linker is attached to an oligo at 5â and 3â end [Internet]. Biosynthesis; 2018 [cited Apr. 17, 2026]. Available from: https://www.biosyn.com/faq/Can-you-show-me-how-thiol-linker-is-attach-to-an-oligo-at-5-and-3-end.aspx (Year: 2018).*

(Continued)

*Primary Examiner* — Nancy J Leith
*Assistant Examiner* — Emma R Hoppe
(74) *Attorney, Agent, or Firm* — NSIP Law

(57) ABSTRACT

The present invention relates to: a single nanoparticle biosensor platform comprising a metal nanoparticle in which a biomolecule is immobilized between two metal nanoseeds, and a biosensor comprising same; a method for detecting mutations by using the biosensor; and a method for manufacturing a single nanoparticle biosensor platform, comprising a step of forming a metal nanoparticle in which a biomolecule is immobilized between two metal nanoseeds. The single nanoparticle biosensor platform according to the present invention enables high sensitivity and reliability detection of a target, and also enables direct identification of various mutations so as to enable the efficient diagnosis of mutations, thereby being widely usable in the biomedical diagnostic fields and the like.

6 Claims, 20 Drawing Sheets

Specification includes a Sequence Listing.

(56) References Cited

OTHER PUBLICATIONS

Chinese Office Action issued on May 7, 2023, in counterpart Chinese Patent Application No. 201980053469.2 (7 pages in Chinese).

Extended European Search Report issued on Mar. 28, 2022 in corresponding European Patent Application No. 19849511.1 (9 pages in English).

Cho, Minseon, et al., "Detection of mismatched DNAs via the binding affinity of MutS using a gold nanoparticle-based competitive colorimetric method," *Chemical Communications*, 38, 2008 (pp. 4573-4575).

Hu, Jie, et al., "Oligonucleotide-linked gold nanoparticle aggregates for enhanced sensitivity in lateral flow assays," *Lab on a Chip*, 13, 22, 2013 (pp. 4352-4357).

International Search Report issued on Dec. 6, 2019 in counterpart International Patent Application No. PCT/KR2019/010370 (4 pages in English and 4 pages in Korean).

Nam, Jwa-Min, et al. "Plasmonic Nanogap-Enhanced Raman Scattering with Nanoparticles." Accounts of chemical research 49.12, 2016, (10 pages).

Ma, Xingyi, et al. "Gold nanocrystals with DNA-directed morphologies." Nature Communications 7.1, 2016, (8 pages).

Ma, Xingyi, et al. "Single gold-bridged nanoprobes for identification of single point DNA mutations." Nature communications 10.1, 2019, (13 pages).

Chinese Office Action issued on Dec. 26, 2023, in counterpart Chinese Patent Application No. 201980053469.2 (5 pages in English, 5 pages in Chinese).

* cited by examiner

[Fig. 1]
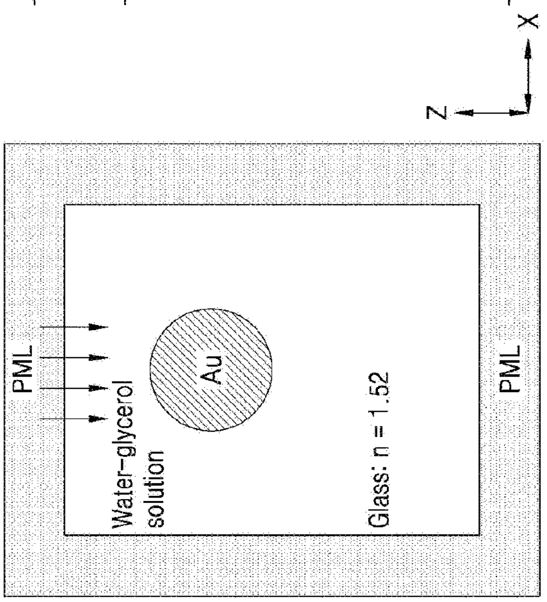
| Glycerol weight (%) | Refractive index | Difference for 1% |
|---|---|---|
| 80 | 1.44290 | 0.00155 |
| 60 | 1.41299 | 0.00149 |
| 40 | 1.38413 | 0.00135 |
| 20 | 1.35749 | 0.00130 |
| 0 | 1.33300 | - |

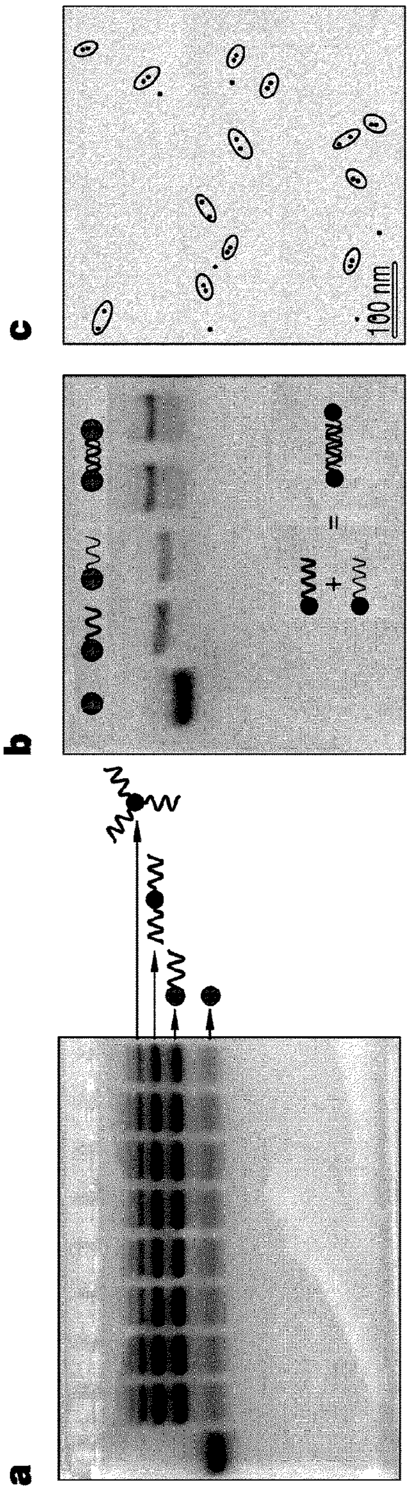
[Fig. 2]

[Fig. 3]
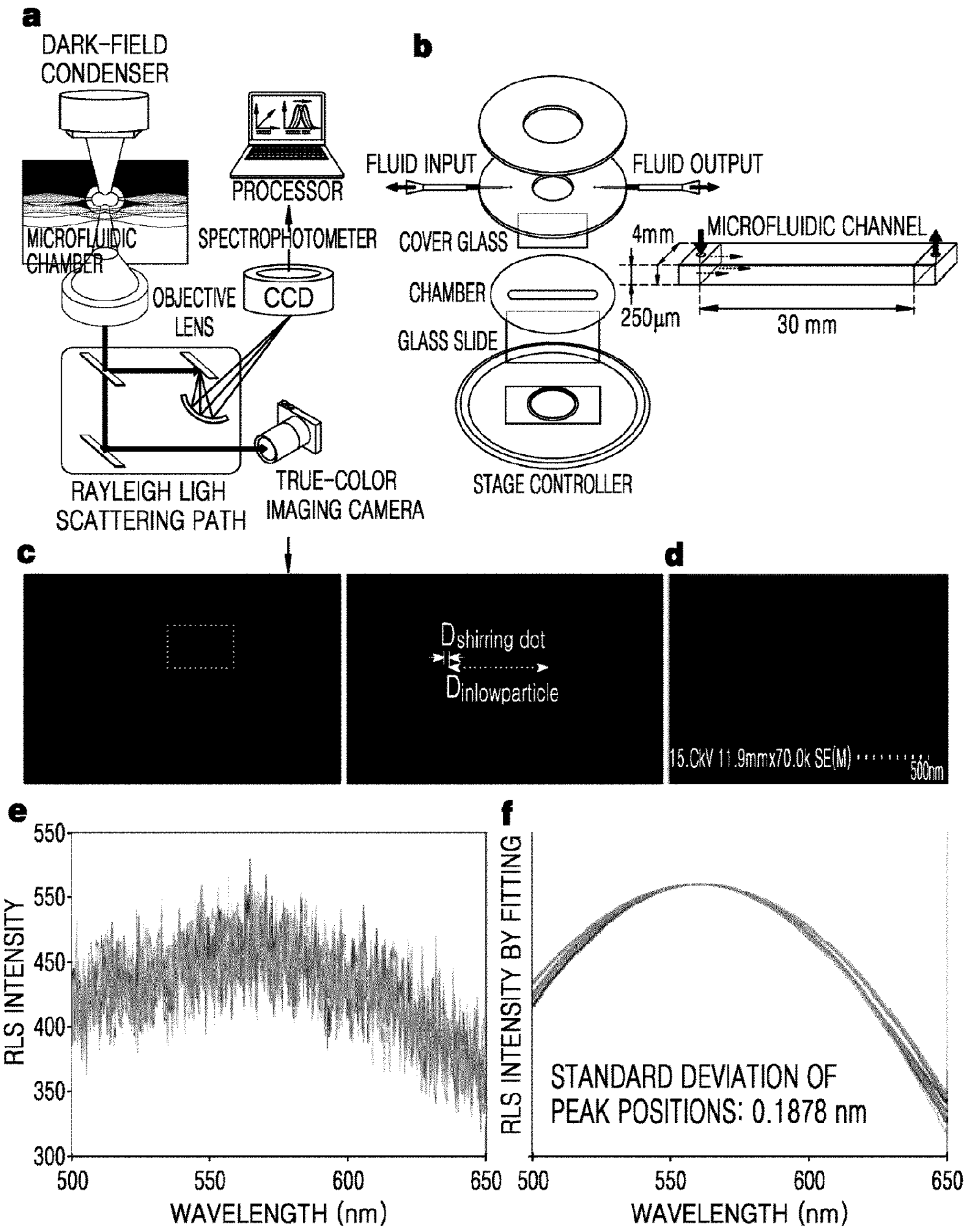

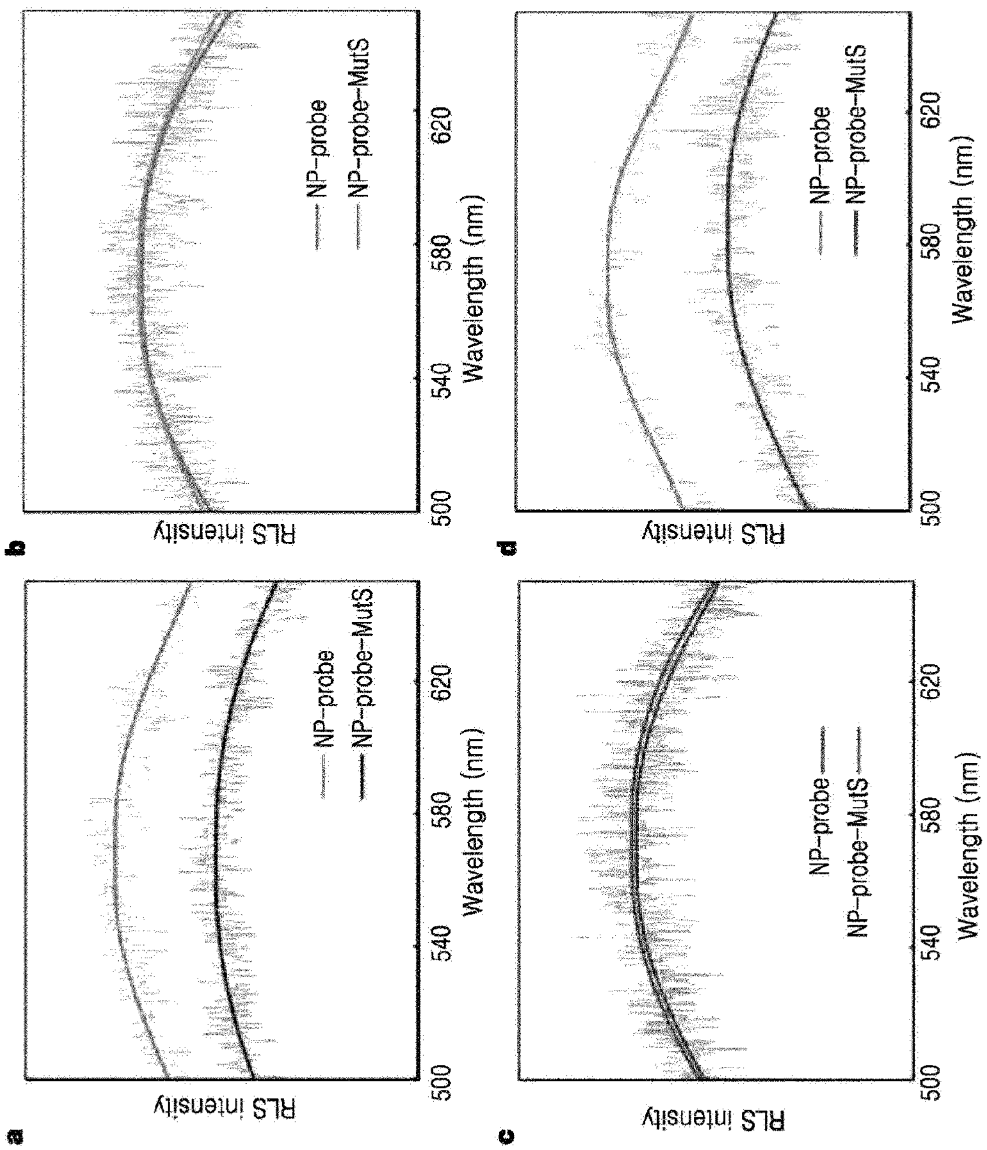
[Fig. 4]

MCF7

Sty I ... Alu I

CCACCAAGGTCCAAAGCGAGCAAGAGAATCCCAGGACAGAAAGGTAAAGCT SEQ ID NO: 14

GGTGGTTCCAGGTTTCGCTCGTTCTCTTAGGGTCCTGTCTTTCCATTTCGA SEQ ID NO: 15

MCF1937

Sty I ... Alu I

CCACCAAGGTCCAAAGCGAGCAAGAGAATCCCCAGGACAGAAAGGTAAAGCT SEQ ID NO: 16

GGTGGTTCCAGGTTTCGCTCGTTCTCTTAGGGGTCCTGTCTTTCCATTTCGA SEQ ID NO: 17

MCF7

Mbo I ... Sty I

TGGGGATCCAGGGTGTCCACCCAATTGTGGTTGTGCAGCCAGATGCCTGGACAGAGGACAATGGCTTCCATGGT SEQ ID NO: 18

ACCCCTAGGTCCCACAGGTGGGTTAACACCAACACGTCGGTCTACGGACCTGTCTCCTGTTACCGAAGGTACCA SEQ ID NO: 19

SNU251

Mbo I ... Sty I

TGGGGATCCAGGGTGTCCACCCAATTGTGGTTGTGCAGCCAGATGCCTGAACAGAGGACAATGGCTTCCATGGT SEQ ID NO: 20

ACCCCTAGGTCCCACAGGTGGGTTAACACCAACACGTCGGTCTACGGACTTGTCTCCTGTTACCGAAGGTACCA SEQ ID NO: 21

【Fig.5】

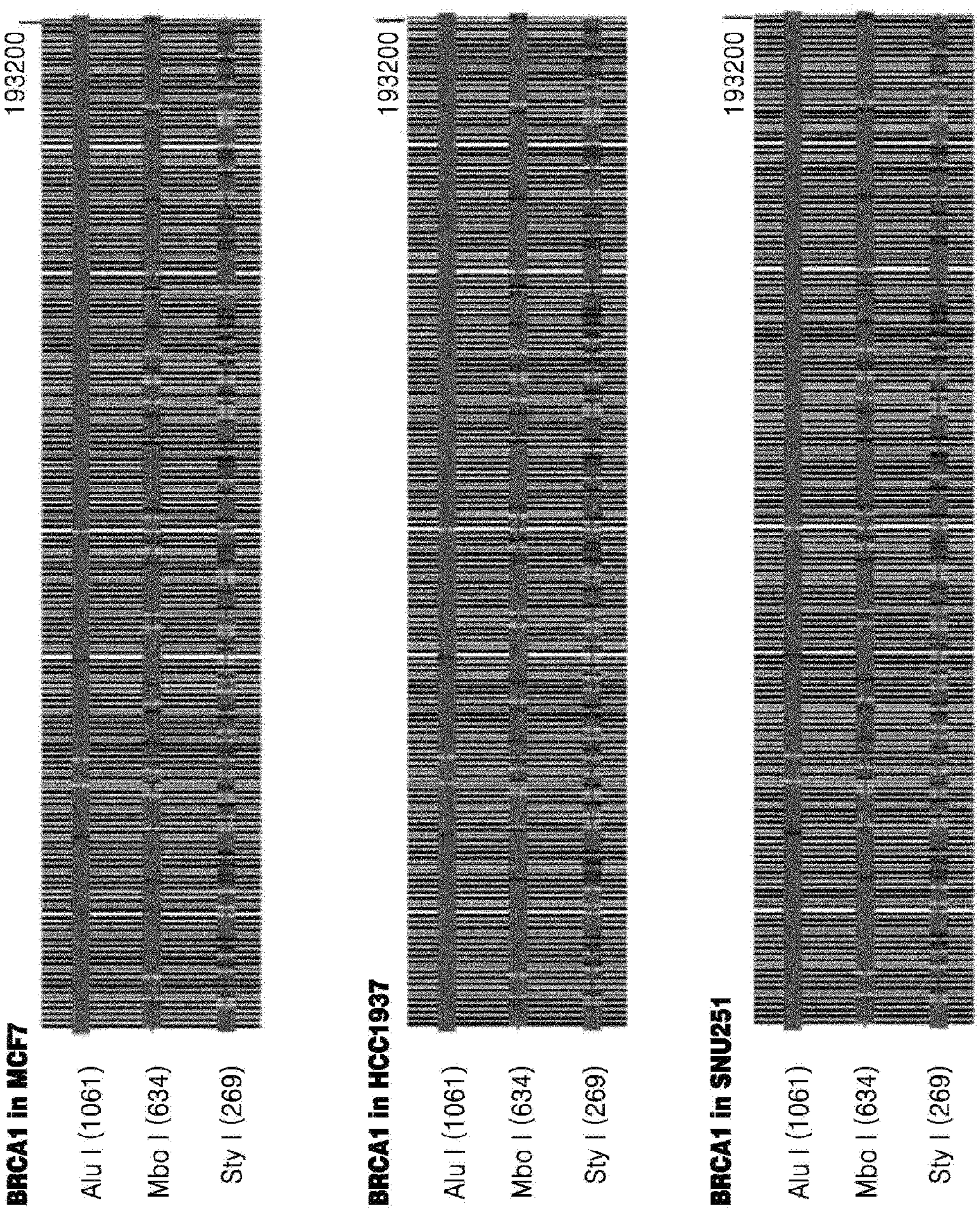
[Fig. 6]

[Fig. 7]
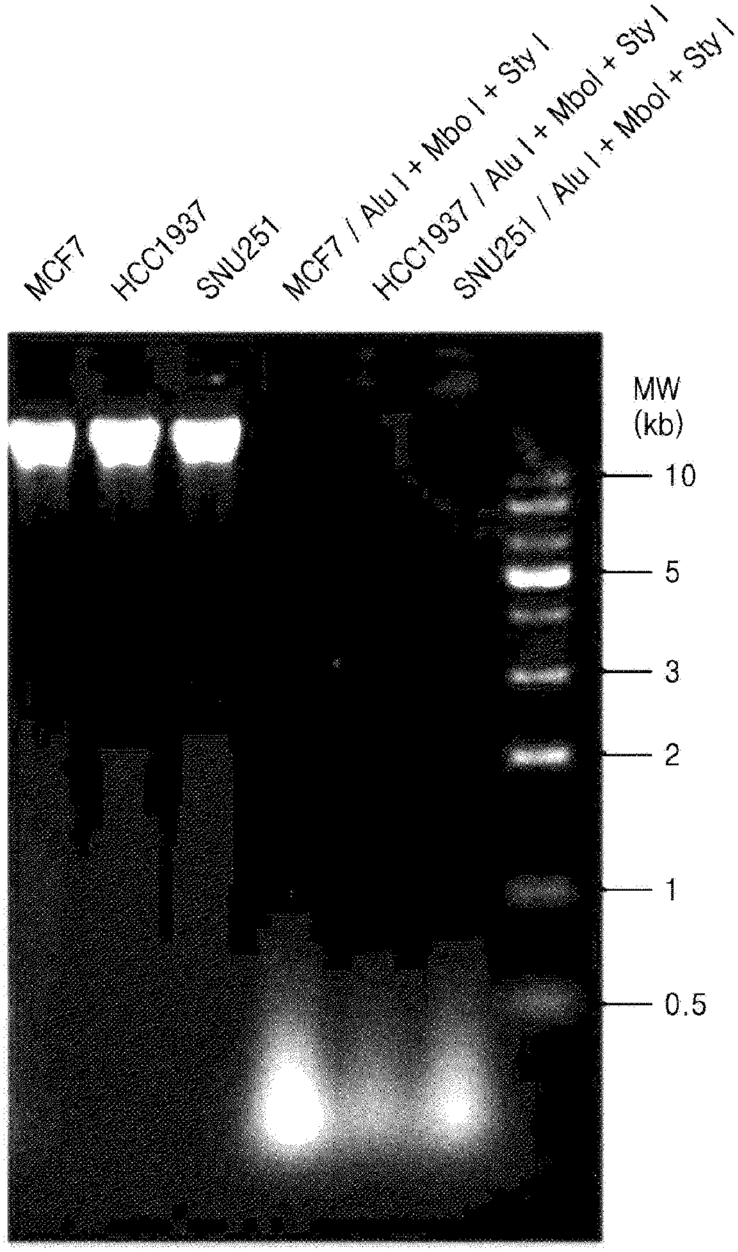

[Fig. 8]
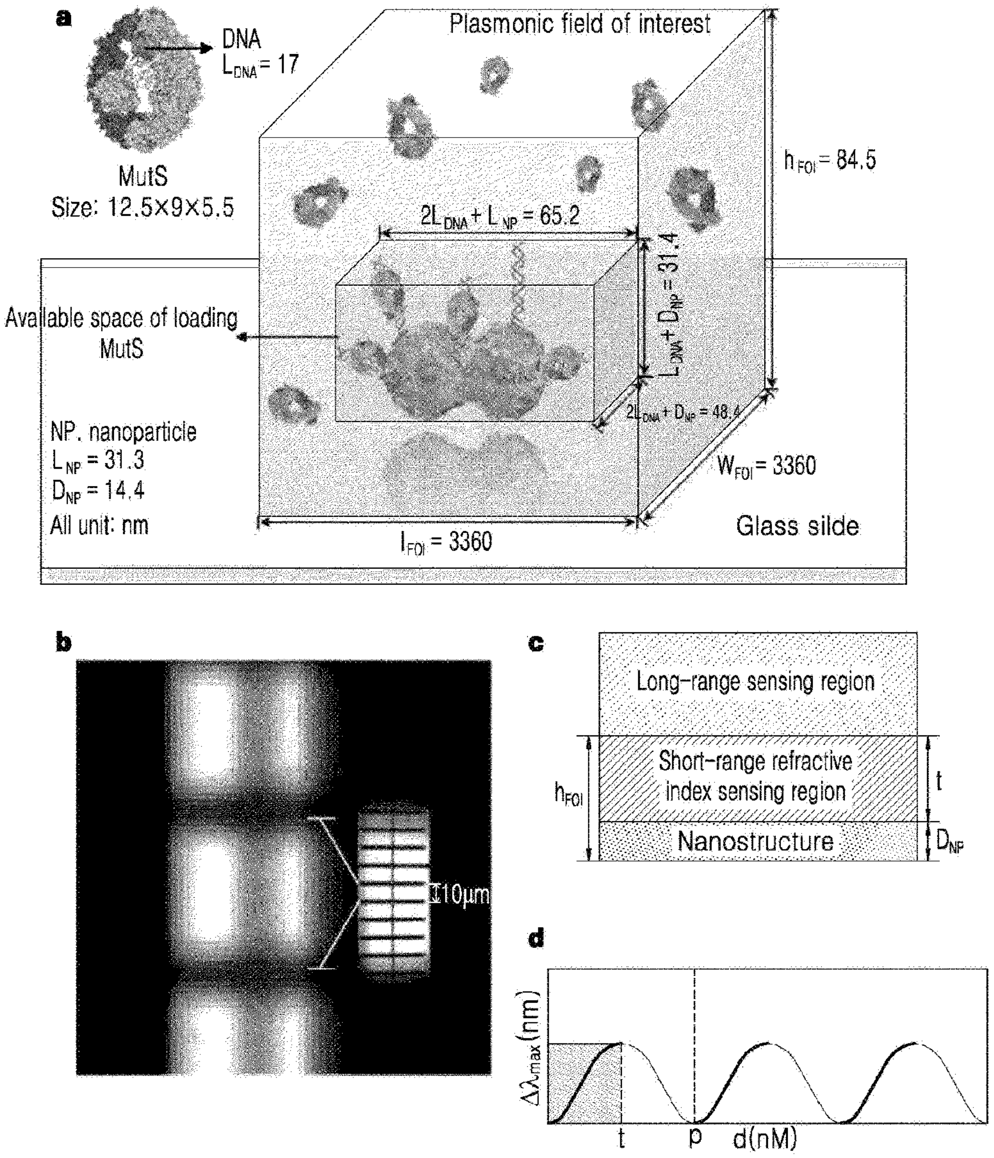

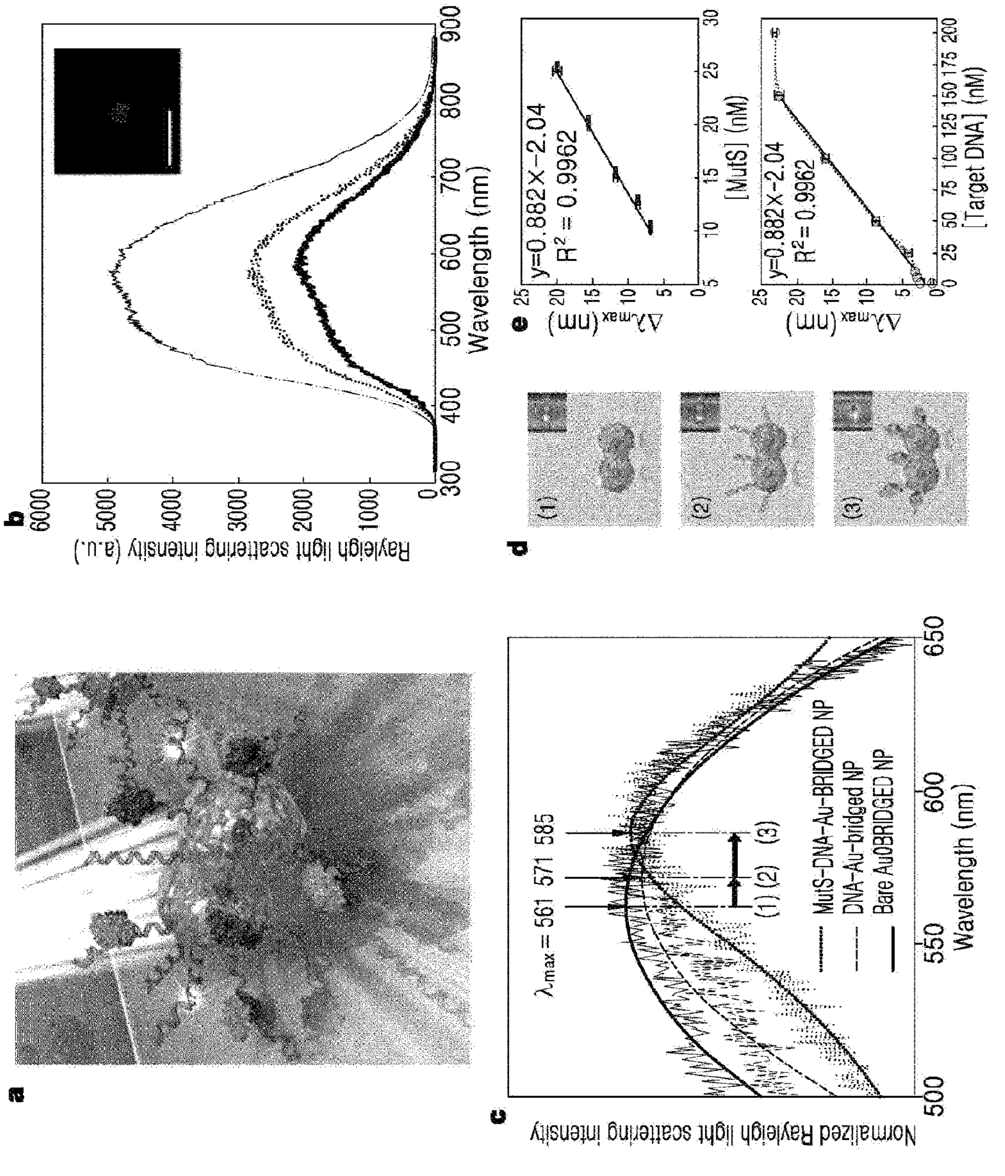
[Fig. 9]

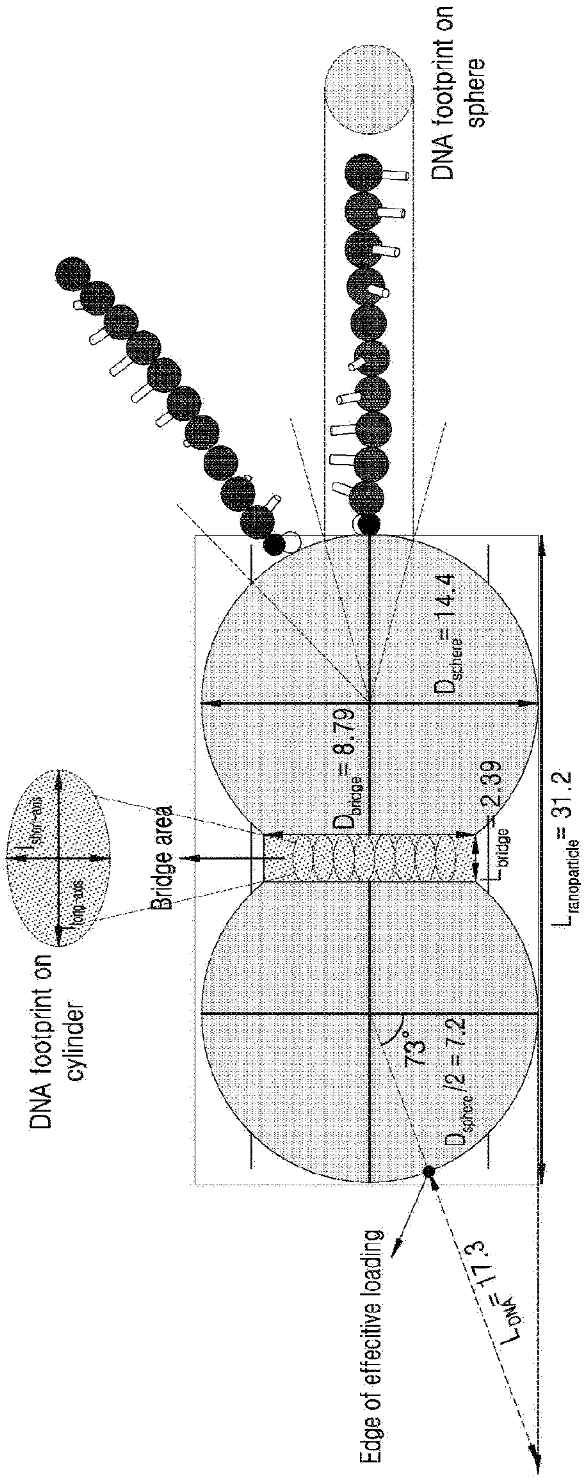
[Fig. 10]

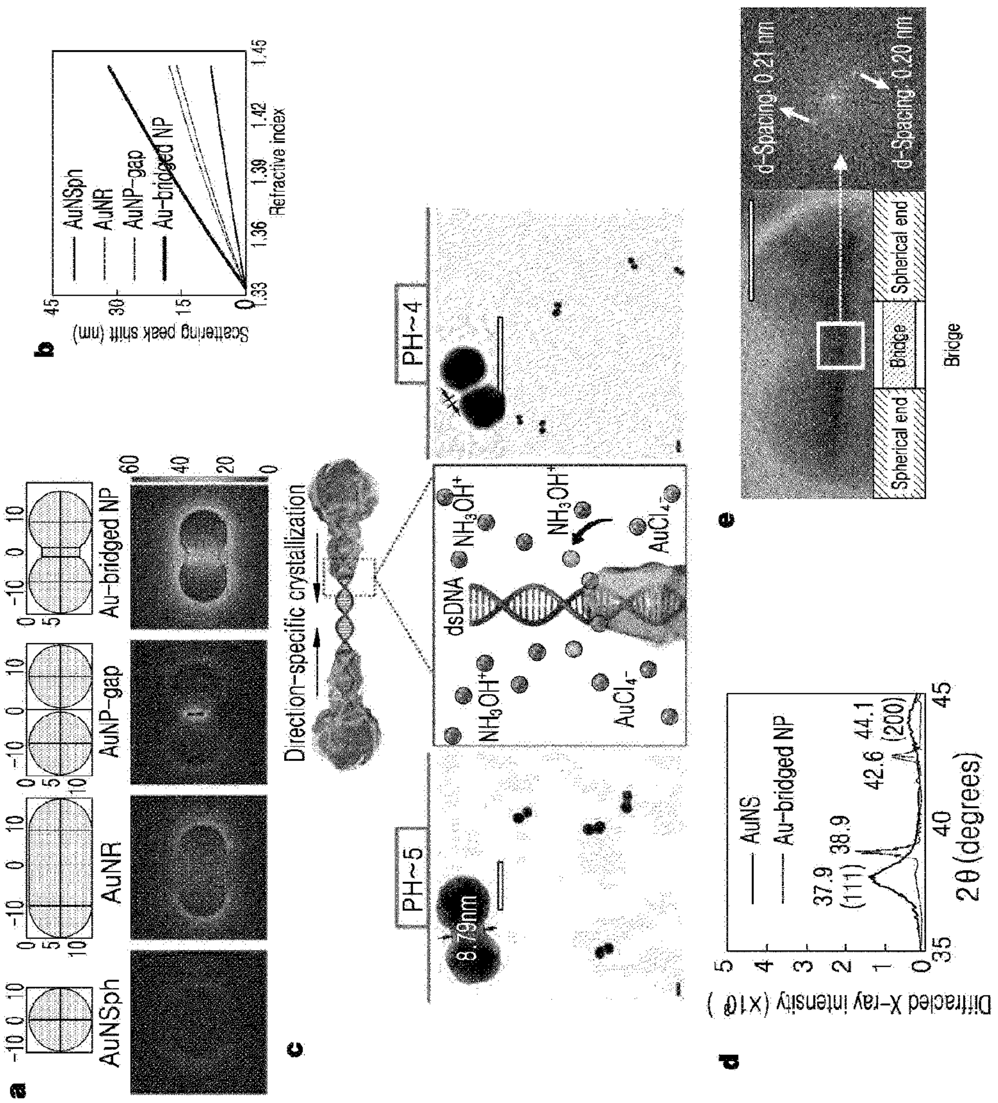
[Fig. 11]

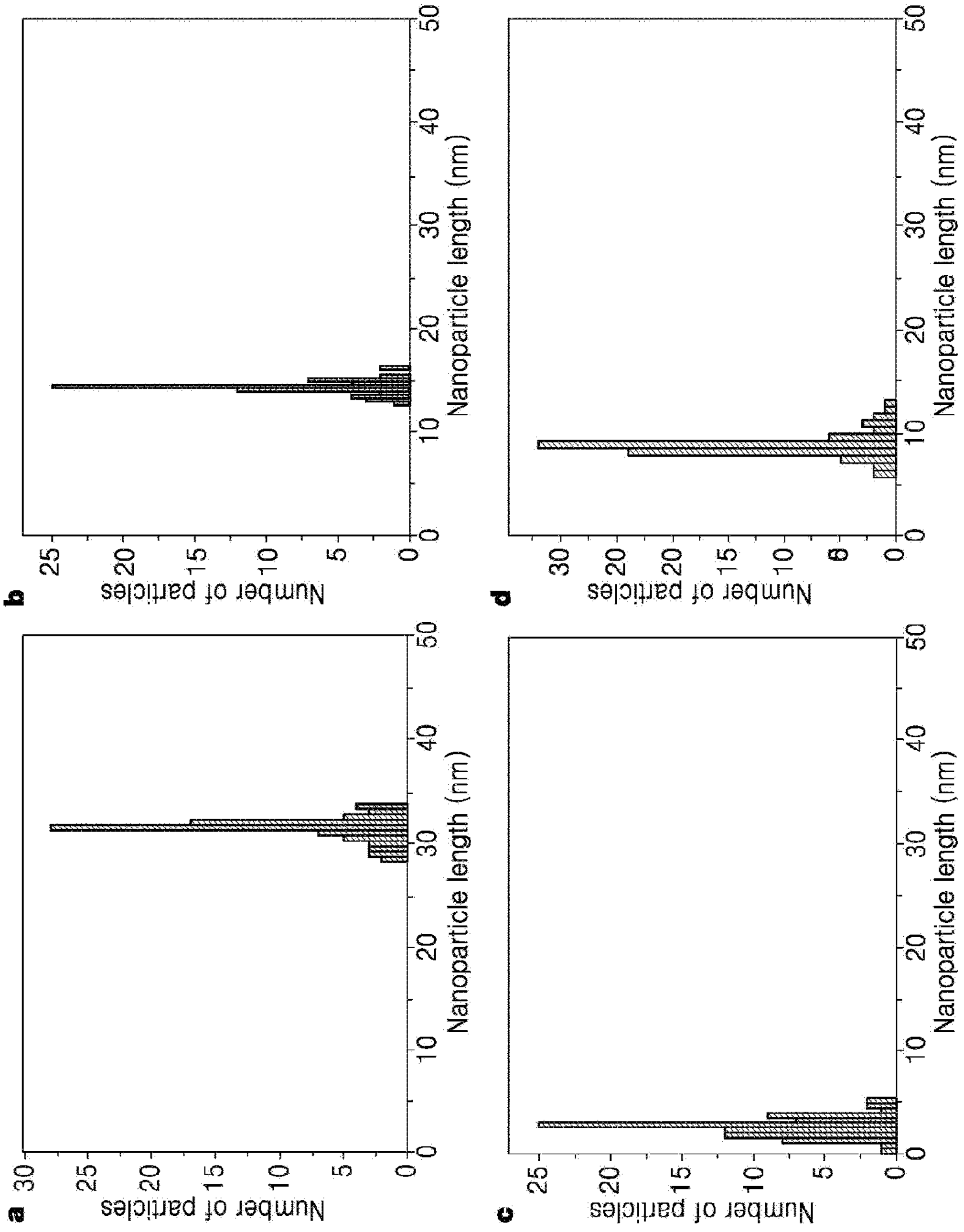
[Fig. 12]

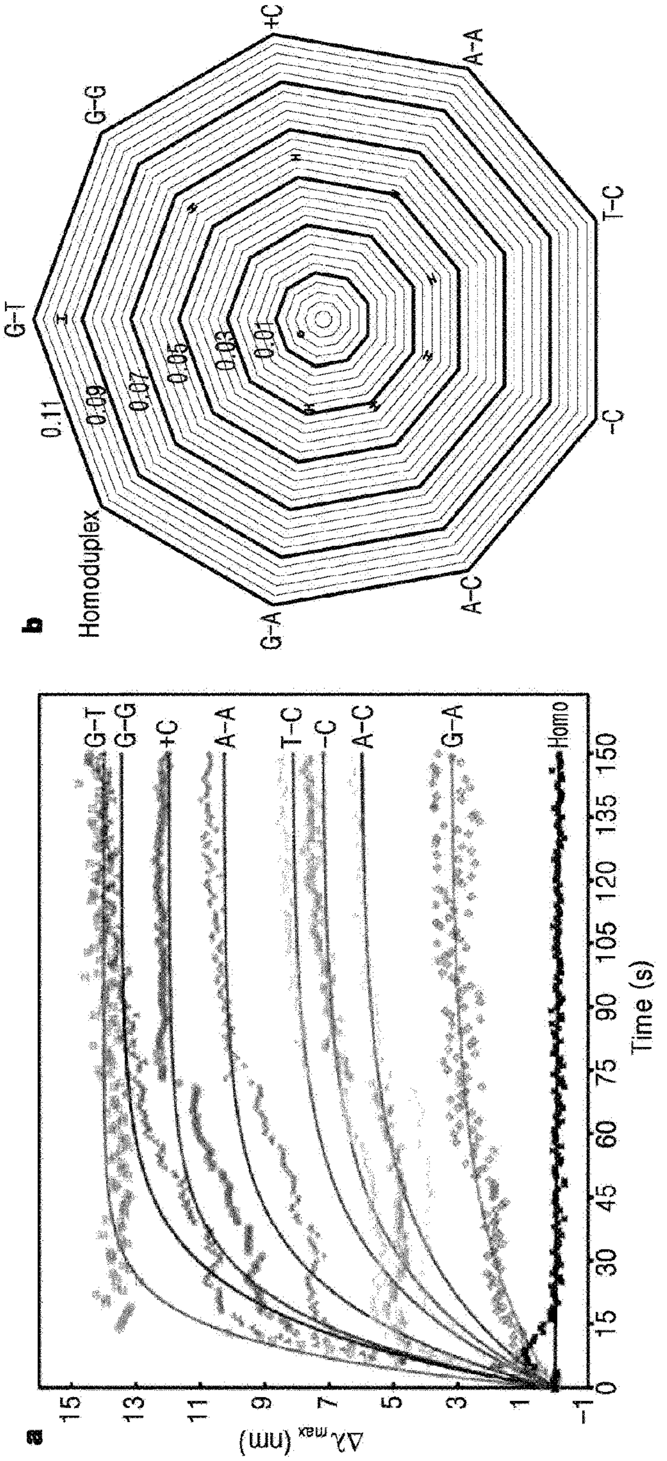
[Fig. 13]

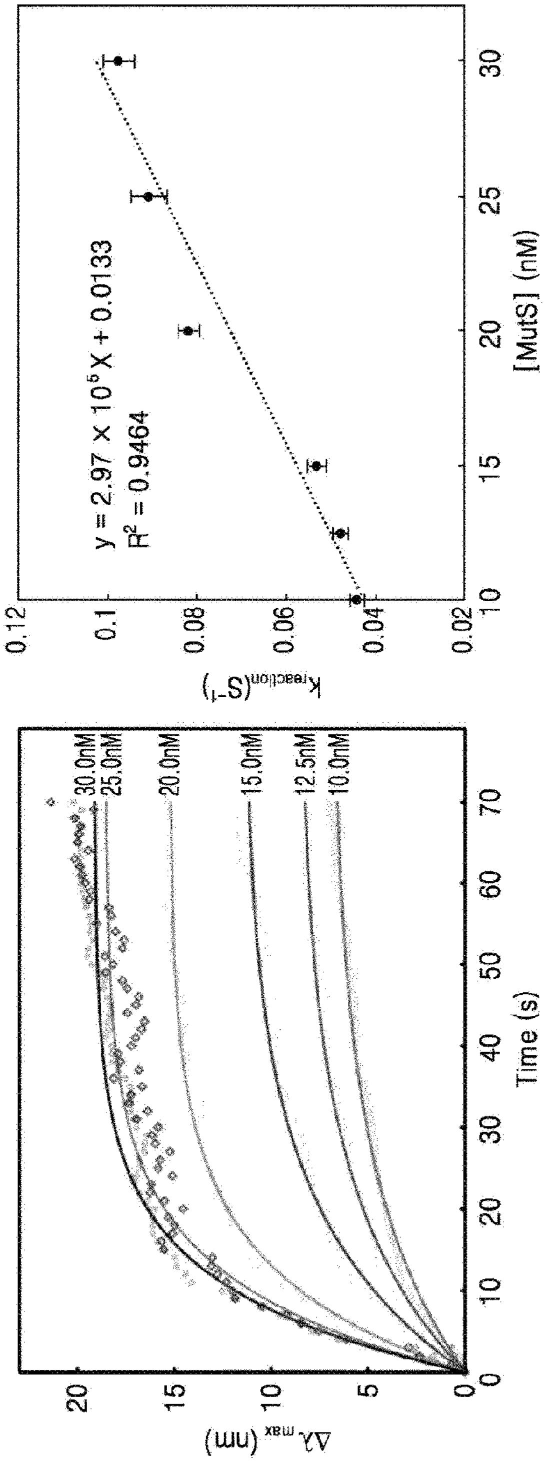
[Fig. 14]

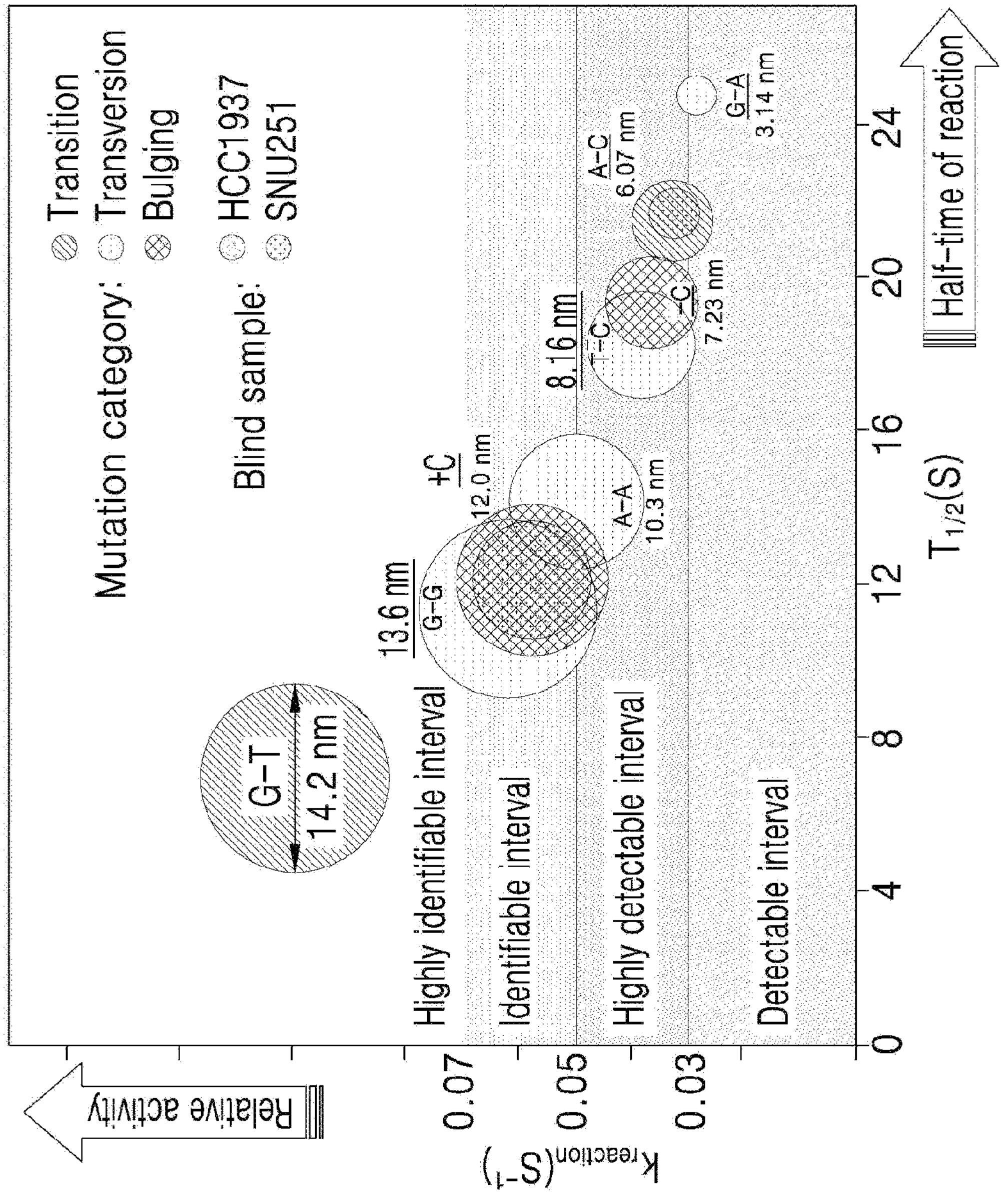
[Fig. 15]

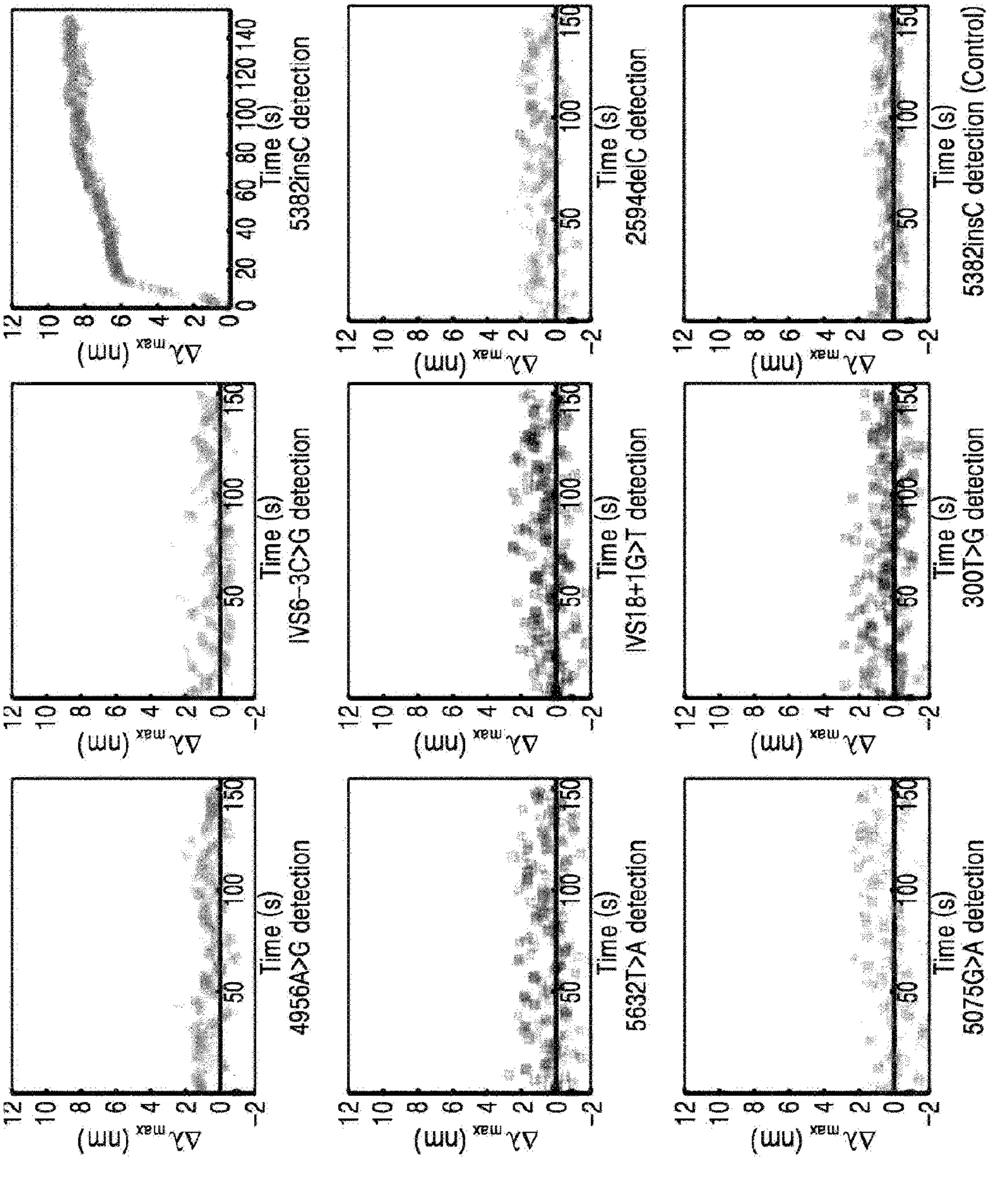
[Fig. 16]

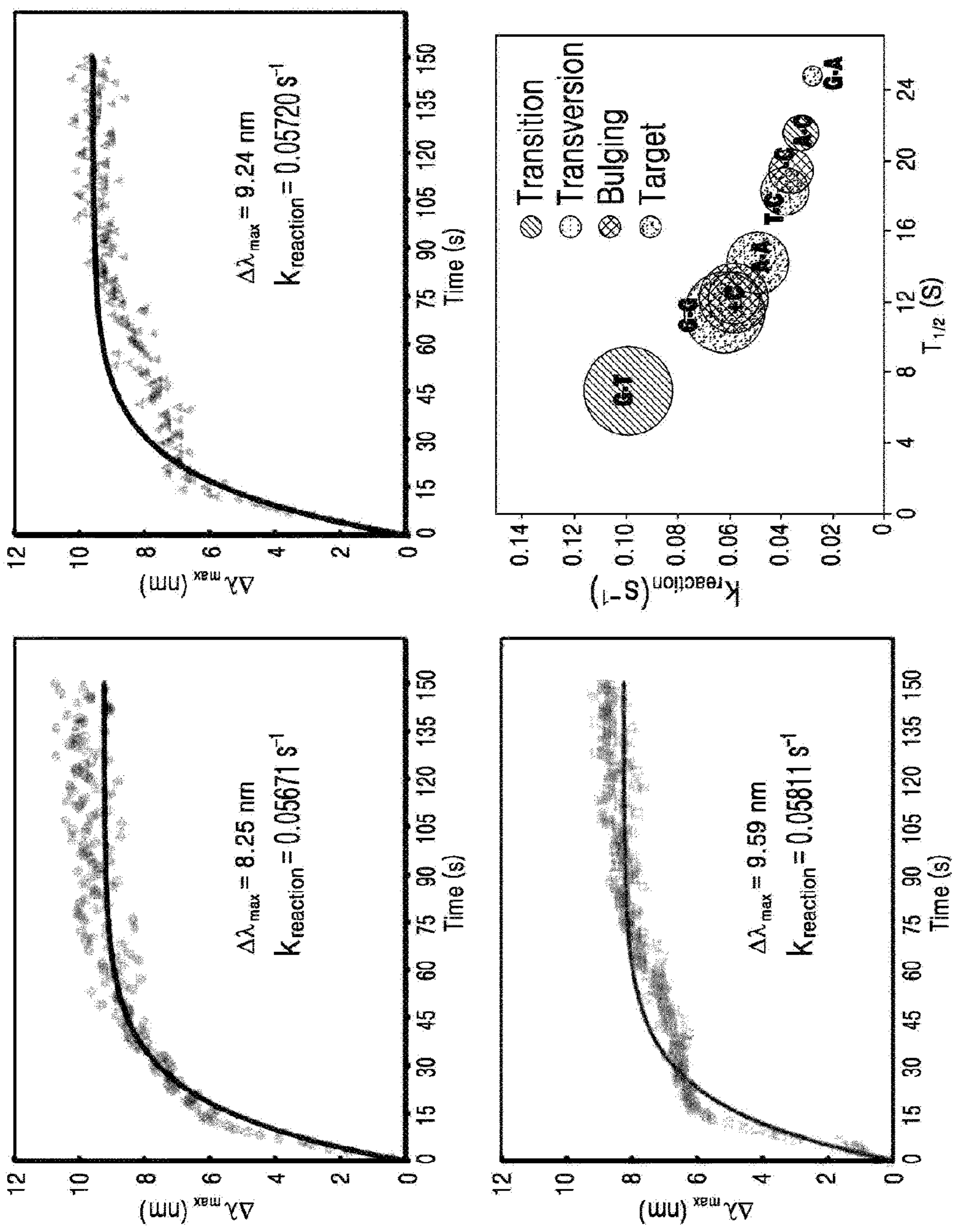
[Fig. 17]

[Fig. 18]
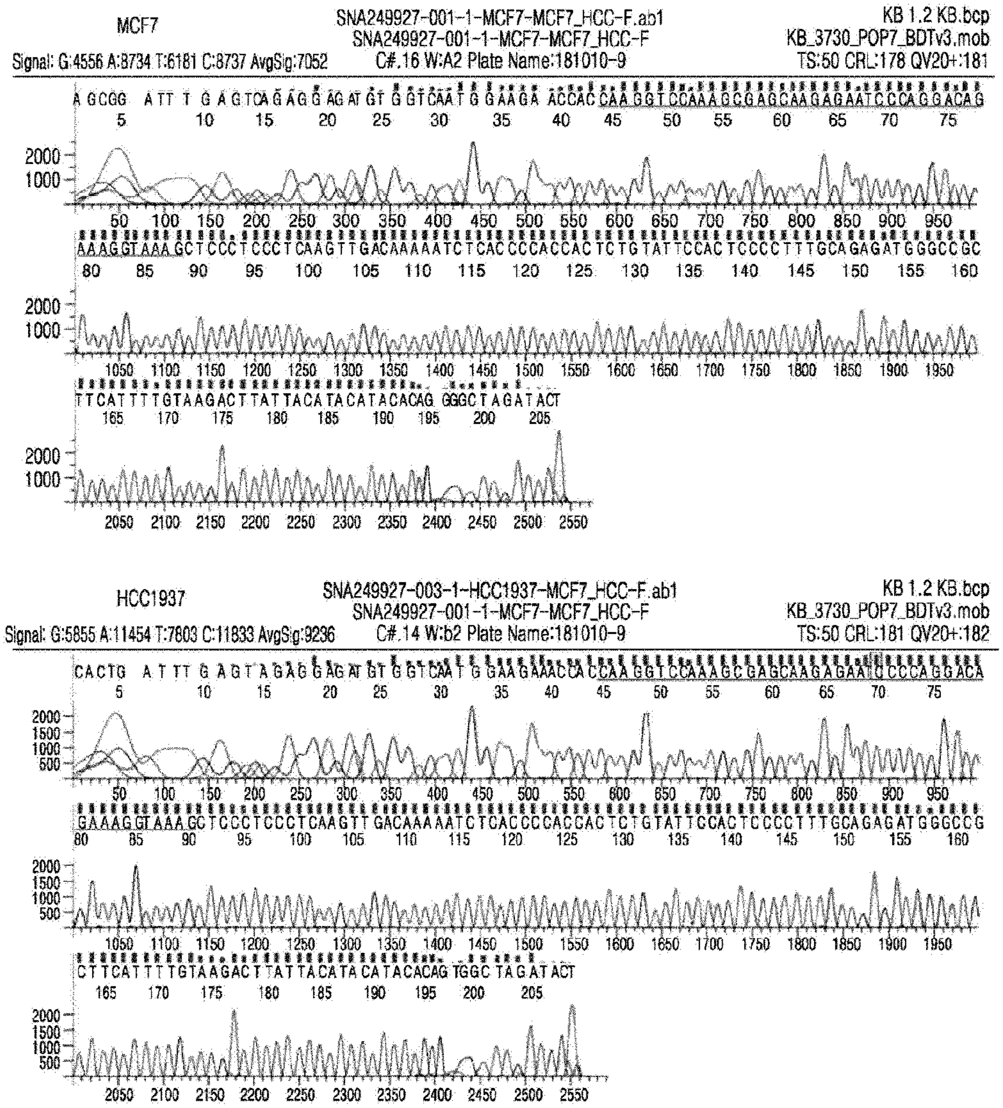

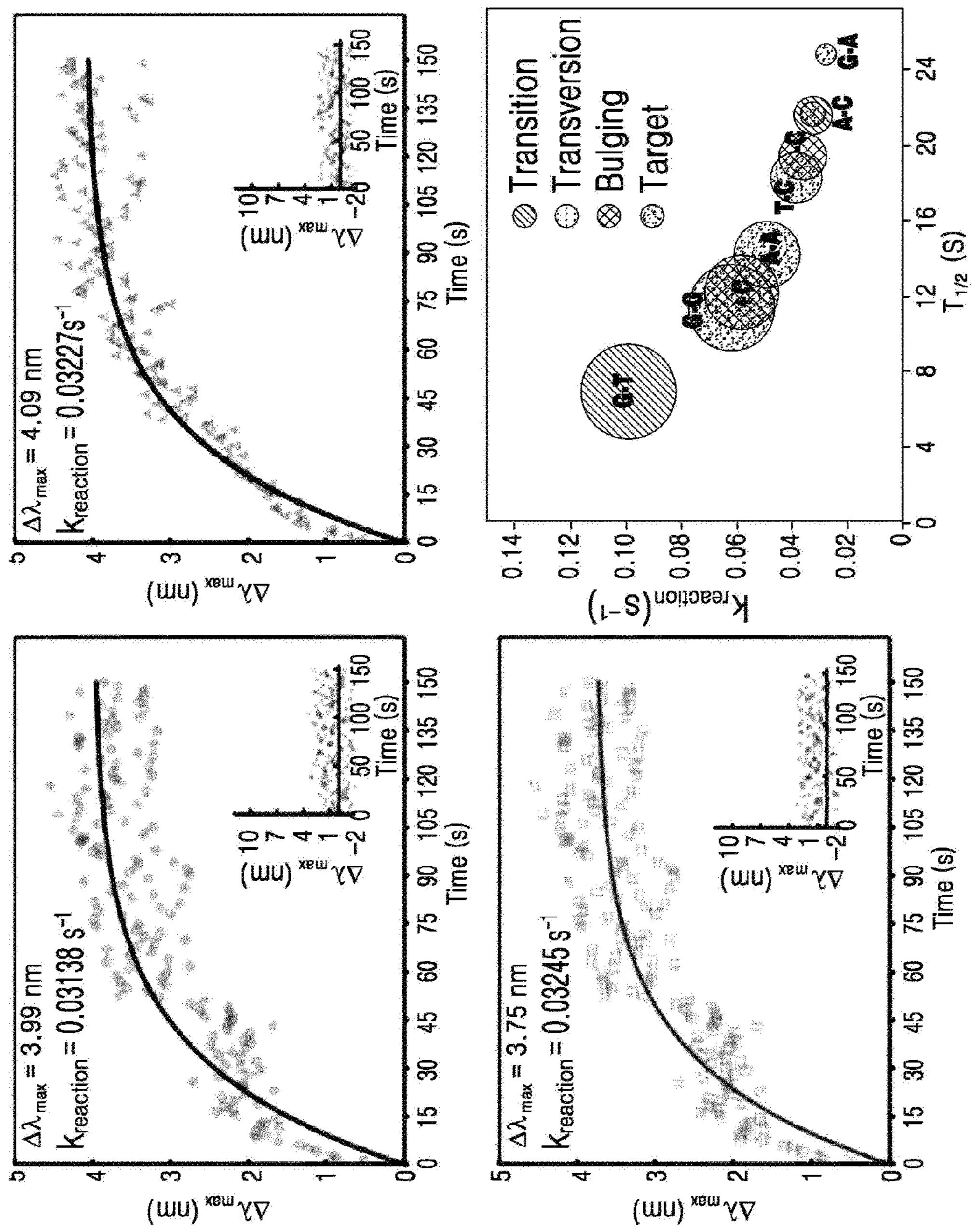
[Fig. 19]

[Fig. 20]
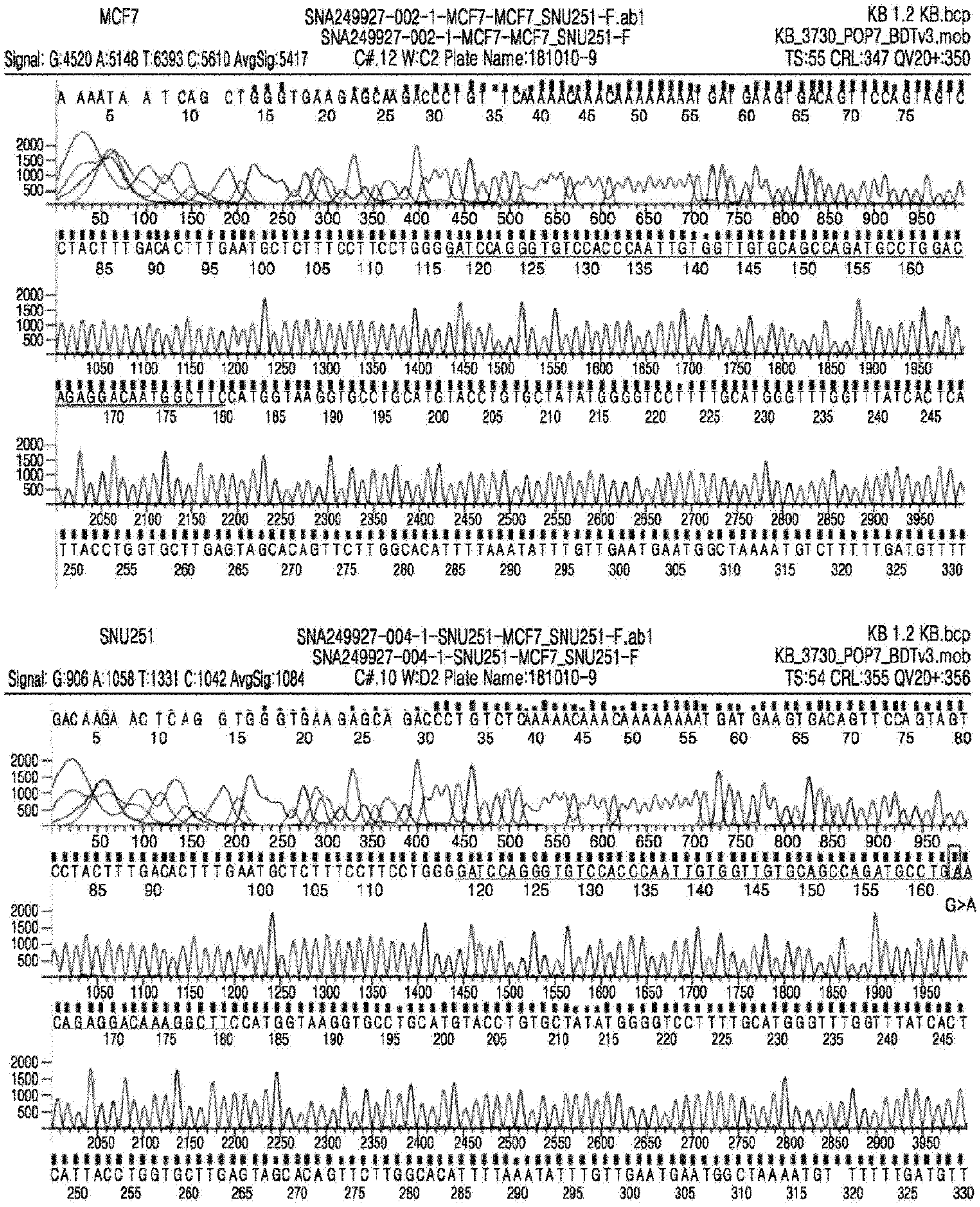

METHOD FOR SYNTHESIZING SINGLE METAL NANOBRIDGED STRUCTURE AND METHOD FOR MANUFACTURING DNA POINT MUTATION DETECTION SENSOR BY USING SAME

CROSS REFERENCE TO RELATED APPLICATIONS

This application is a U.S. National Stage Application of International Application No. PCT/KR2019/010370, filed on Aug. 14, 2019, which claims the benefit under 35 USC 119(a) and 365(b) of Korean Patent Application No. 10-2018-0095140, filed on Aug. 14, 2018 and Korean Patent Application No. 10-2019-0099454, filed on Aug. 14, 2019, in the Korean Intellectual Property Office, the entire disclosure of which is incorporated herein by reference for all purposes.

INCORPORATION-BY-REFERENCE OF MATERIAL SUBMITTED BY U.S.P.T.O. PATENT CENTER

This application contains a Sequence Listing, which is being submitted in computer readable form via the United States Patent and Trademark Office Patent Center and which is hereby incorporated by reference in its entirety for all purposes. The txt file submitted herewith, which is named as "MISC20210628_0181590024_SequenceList.txt" and is created on Jul. 27, 2021, contains a 5,084 bytes file.

TECHNICAL FIELD

The present invention relates to a single nanoparticle biosensor platform including a metal nanobridge structure and a method for constructing the same. More specifically, the present invention relates to a single nanoparticle biosensor platform including metal nanoparticles, each of which consists of two metal nanoseeds and a biomolecule anchored between the metal nanoseeds, a biosensor including the single nanoparticle biosensor platform, a method for detecting mutations using the biosensor, and a method for constructing the single nanoparticle biosensor platform including forming metal nanoparticles, each of which consists of two metal nanoseeds and a biomolecule anchored between the metal nanoseeds.

BACKGROUND ART

Many diseases have a genetic component; their detections therefore require a clear understanding of metabolic disorders caused by mutations for biomedical diagnostics. Most methods for diagnosing gene mutations rely on sequencing, but an optimal method for acquiring mutation information can determine the presence and identity of mutant bases without prior knowledge of the sequence, ideally without artifacts from labels and the in vitro environment. An effort has been made to find such a method with a system opposite to postreplicative mismatch repair (MMR) in many organisms, where the mismatch repair (MMR) initiation protein MutS recognizes mutations in a sequence non-specific manner depending on the introduction of other enzymes that repair MutL and mutant DNA, by a nanoplasmonic biosensor (Ma, X., Truong, P L, Anh, N. H. & Sim, S. J. Biosensors & Bioelectronics 67, 59-65 (2015)).

The reliability of nanobiosensing is generally determined by two main factors: nanomaterials for single generation and biomolecules for target recognition that are directly associated with detection sensitivity and selectivity for specific physical conditions. Among these nanomaterials, plasmonic nanoparticles have attracted interest due to their ability to interact with incident light and produce localized surface plasmon resonance (LSPR). The collective oscillation of electrons in the nanostructure at a given resonant frequency transduces changes in the local refractive index (RI) into shifts in the plasmonic bands of their absorption and scattering spectra. The sensing scale can be reduced to a single nanoparticle, contributing to single-nanoparticle sensing (sNPS); such single NP sensing (sNPS) can relay local biological information on a nanometer scale in which the limit of detection (LOD) reaches countable numbers of molecules using a very small sensing volume. In contrast, most other sensing techniques using bulk solutions or planar surfaces show a limited ability to localize and separate sensing elements and are limited by slow molecular diffusion, stochastic binding, and frequent dissociation of complexed biomolecules with consequent disequilibrium of reactions, resulting in signal fluctuations with a low signal-to-noise ratio (S/N). An sNPS sensor is a tiny probe capable of high-throughput and parallel readout in which the structure and localized sensing volume/area of the NP are essential for RI sensitivity. Systematic studies on the RI sensitivity of gold nanoparticles (NPs) with different shapes have shown that rod-like NPs exhibit the highest sensitivity to changes in RI (Truong, P. L., Ma, X. & Sim, S. J. Nanoscale 6, 2307-2315 (2014)). It has recently been demonstrated that, apart from the particle shapes, nanogap and nanobridge structures are associated with and generate strong optical signals by plasmonic coupling, further enhancing the local field to generate distinct spectral response; (Lim, D. K., et al. Nature Nanotech. 6, 452-460 (2011); Nam, J. M., Oh, J. W., Lee, H. & Suh, Y. D. Acc. Chem. Res. 49, 2746-2755 (2016)). However, synthesizing colloidal plasmonic NPs with a predefined structure is challenging due to the difficulty in manipulating atoms that are transient in solution. Moreover, chemically synthesized NPs are restricted to a highly symmetric shape with identical surface facets (e.g., nanospheres, nanorods, nanocubes, nanodisks, and others). The structural programmability of NPs could provide a powerful means to overcome sNPS limitations in sensitivity and reproducibility. Two research groups recently achieved breakthroughs in synthesis-by-design, at, sub-5 nm precision using a programmable biomolecule, i.e., DNA, to create well-defined nanoplasmonic particles either by casting in DNA molds (Sun, W., et al. Science 346, 1258361 (2014)) or using DNA frameworks (Ma, X., et al. Nat Commun 7, (2016)).

sNPS provides a variety of applications that make use of most of its intrinsic small sensing volume comparable to the size of biomolecules such as nucleic acids or proteins. For example, the MutS protein is 125×90×55 Å; thus, adsorption of MutS onto a single NP can drastically alter the collective oscillatory behavior of its surface electrons, resulting in wavelength shifts in the NP spectra. Since single point mutations are not substantially recognized based on PCR and other DNA chip-based assays, the specificity of the biological interaction of MutS including mismatched DNA has promoted studies on nucleotide polymorphisms. The most extensive studies are based on single-molecule fluorescence resonance energy transfer (smFRET); however, these require labor-intensive steps such as labeling of MutS or fabrication of radioactive probes for DNA. Recent studies using single-molecule imaging by atomic force microscopy are very complicated and almost impossible to apply to biomedical diagnostics. On the other hand, bulk measurements of single point mutations by gel mobility shift assay, filter/chip binding assay, nuclease protection assay, surface plasmon resonance (SPR), electrochemical assay, and quartz crystal microbalance (QCM) do not output real-time information on molecular interactions and are inefficient and time consuming.

Thus, the inventors of the present invention have earnestly and intensively conducted research to solve the problems of the prior art. As a result, the inventors have succeeded in preparing Au-bridged nanoparticles with high RI sensitivity by modifying both ends of each DNA molecule so as to bind to gold nanoseeds and crystallizing the gold in two opposite directions and have found that a single nanoparticle biosensor platform including the Au-bridged nanoparticles can be used to detect targets with high sensitivity and reliability and directly identify various mutations depending on the relative activity of MutS for the mutations. The present invention has been accomplished based on this finding.

DETAILED DESCRIPTION OF THE INVENTION

Problems to be Solved by the Invention

One object of the present invention is to provide a single nanoparticle biosensor platform including a metal nanobridge structure and a biosensor including the single nanoparticle biosensor platform.

A further object of the present invention is to provide a method for detecting mutations using the biosensor.

Another object of the present invention is to provide a method for constructing the single nanoparticle biosensor platform including forming metal nanoparticles, each of which consists of two metal nanoseeds and a biomolecule anchored between the metal nanoseeds, and creating a metal nanobridge structure using the metal nanoparticles.

Means for Solving the Problems

The present invention provides a single nanoparticle biosensor platform including a metal nanobridge structure and a biosensor including the single nanoparticle biosensor platform.

The present invention also provides a method for detecting mutations using the biosensor.

The present invention also provides a method for constructing the single nanoparticle biosensor platform including forming metal nanoparticles, each of which consists of two metal nanoseeds and a biomolecule anchored between the metal nanoseeds, and creating a metal nanobridge structure using the metal nanoparticles.

Effects of the Invention

The single nanoparticle biosensor platform of the present invention can be used to not only detect targets with high sensitivity and reliability, but also to directly identify various mutations, enabling efficient diagnosis of mutations. Therefore, the single nanoparticle biosensor platform of the present invention can be utilized in a wide range of fields, including biomedical diagnostics.

BRIEF DESCRIPTION OF THE DRAWINGS

FIG. 1 shows a schematic illustration of RI sensitivity analysis of single NPs. LSPR wavelength shifts in response to changes in RI of the surrounding medium. The table on the right shows the RI values for the medium.

FIG. 2 shows preparation and characterization of AuNS-dsDNA-AuNS: a Image of a gel of different AuNS-ssDNA conjugates separated by electrophoresis. Each band represents a certain number of ssDNAs anchored to one AuNS. The leftmost band shows the bare nanoseed without binding of DNA; b Image of a gel of AuNS-dsDNA-AuNS separated and identified by electrophoresis after ssDNA hybridization; and c TEM image of AuNS-dsDNA-AuNS.

FIG. 3 shows an sNPS system: a Detailed configuration of the sNPS system based on RLS and LSPR of single Au-bridged NPs by white-light irradiation; b Schematic diagram of the detection chamber, c Image of the chamber acquired by the camera. Individual nanoparticles with inter-particle spacing ~5-fold greater than the diameter of shinning dots were position-marked and analyzed; d SEM image of the chamber; e Raw spectra of an Au-bridged NP acquired once per minute for 10 min; and f Lorentzian fitting of the 10 raw spectra demonstrated a peak measurement precision of 0.188 nm.

FIG. 4 shows sensing specificity: a Control experiment of MutS with probes. RLS spectra of a single NP showed no significant $\lambda_{max}$ shift (0.356 nm blue-shift); b Control experiment of MutS with homoDNA showing 0.343 nm red-shift in $\lambda_{max}$; c Control experiment of mutant target DNA (mDNA) with nonspecific components in serum. RLS spectra showed no significant $\lambda_{max}$ shift (0.700 nm red-shift); d Introduction of MutS into the serum significantly generated a 14.7-nm red-shift under the same detection conditions as in c.

FIG. 5 shows sequences showing the active sites of the restriction enzymes. MboI, 5'-GATC-3'; AluI, 5'-AGCT-3'; StyI, 5'-CCWWGG-3'.

FIG. 6 shows computed fragmentation maps of BRCA1 of different cell lines after restriction digestion by enzymes MboI, AluI and StyI. The software GENETYX 4.0 (Genetyx Corporation, Tokyo, Japan) was used for the analysis.

FIG. 7 shows the results of agarose gel electrophoresis of BRCA1 DNA before and after synergetic digestion by three restriction enzymes (DNA ladder shown in the rightmost). The genomic DNA was extracted from breast cancer cell lines MCF7 and HCC1937, and an ovarian cancer cell line SNU251.

FIG. 8 shows the plasmonic field of interest (FOI) of an individual nanoparticle: a Schematic diagram of the FOI and the available space for loading MutS of an Au-bridged NP; b Scale calibration of the CCD images. The length of one pixel is equal to 0.42 μm; c Illustration of height (h) of the FOI; and d Illustration of the periodicity of LSPR peak shifts. The region marked in green color is the short-range refractive index sensing region where the equation, $\Delta\lambda_{max}$=mΔn[1-exp(−2d/L)], can be used to describe LSPR wavelength shift as a function of the medium concentration changes. Since this equation does not apply to long-range LSPR sensing, the schematic curve does not consider real profiles of the oscillation behavior in the long-range LSPR (e.g., inharmonic properties).

FIG. 9 shows the fabrication of single nanoparticle (NP) biosensor of high sensitivity and fidelity: a Schematic illustration of sNPS for identifying single point DNA mutations; b Representative Rayleigh light scattering (RLS) spectra and in-situ dark-field microscopy image of an Au-bridged NP. Scale bar, 1 μm; c Localized surface plasmon resonance (LSPR) $\lambda_{max}$ shifts upon binding of DNA and MutS. Same line legend for (b, c); d Each step of molecular binding (1, 2, and 3). Insets: real-time images of a single NP obtained with a CCD camera; e Concentration of MutS for adequate signal response. Calibration curve shows the linear relationship between the $\Delta\lambda_{max}$ and various concentrations of MutS; and f LOD of the mutant DNA target. Calibration curve shows the linear relationship between the $\Delta\lambda_{max}$ and various concentrations of target DNA.

FIG. 10 shows estimation of the average loading number of probes (N*) per Au-bridged NP. The nanoparticle was modeled as two spheres (gray color) bridged by a cylinder (yellow color); the DNA footprints were assumed to be evenly distributed on the particle with the highest loading density and the closest distance from each other, and thus, were modeled as a circular area on the spheres and an ellipse on the cylinder. The ratio of the surface area above the line of "edge of effective loading" to the total area approximates to (180°−73°)/180°=59.4%.

FIG. 11 shows synthesis-by-design of plasmonic nanoparticles (NPs) in solution: a Illustrations of the designed NP models (upper; dimensional unit, nm) and plasmon resonance electric field patterns (below); b Linear fits to localized surface plasmon resonance (LSPR) wavelength shifts vs. changes in the RI of the NP surroundings; c Schematic diagram showing the early stage of direction-specific, contour-following, and shape-controlled crystallization of Au atoms by reducing $AuCl_4^-$ with $NH_3OH^+$. The water interface of DNA provides precise controllability under the synthetic conditions at pH 5 and 4, generating NPs with nanobridges and nanogaps respectively, as shown in the TEM images. Scale bars, 20 nm; d X-ray diffraction spectra of AuNSs and Au-bridged NPs; and e HR-TEM image of the DNA-directed nanocrystal and fast Fourier transform pattern (right) of the selected area. Scale bar, 10 nm.

FIG. 12 shows the size distribution of Au-bridged NPs. Lengths and diameters of the nanostructures were measured using ImageJ. The statistical results demonstrated narrow-sized distributions.

FIG. 13 shows identifiable detection of the eight single point mutations: a Real-time monitoring of MutS binding to each mutant DNA and a homoduplex; and b Replotting of rate constants of interactions between MutS and each point mutation.

FIG. 14 shows reliability of sensing: a Real-time monitoring of MutS at various concentrations binding to GT-mutant DNA; and b Dependence of rate constant on MutS concentration.

FIG. 15 is an atlas of MutS affinities to different point mutations. The atlas was established by single Au-bridged NP sensing a countable number of binding events between MutS and eight different mutations. Diagnostic results for information on the presence and type of potential point mutations in BRCA1 from human breast cancer cells HCC1937 and ovarian cancer cells SNU251 were input into the atlas, predicting mutations of +C and A-C, respectively.

FIG. 16 shows the diagnostic results of BRCA1 point mutation with eight sNPS chips developed in the present invention: a-h The sample from human breast cancer cell line, HCC1937, was detected as the analyte. The sample from MCF7 was used as the control. The clinical samples generated larger $\Delta\lambda_{max}$ values during monitoring. None of the chips yielded an effective $k_{reaction}$ except the 5382insC, indicating that the analyte contains a single cytosine duplication.

FIG. 17 shows the detections of mutations in BRCA1 from cell line HCC1937 using 5382 insC probes. All experiments were performed in triplicate. The $k_{reaction}$ average value (0.0573) was input into the atlas of MutS affinities to different point mutations, predicting mutations of +C in the target.

FIG. 18 shows DNA sequencing results. Compared with the BRCA1 sequence of the cell line MCF7 (negative control without a point mutation), the sequence of HCC1937 exhibited a single cytosine insertion.

FIG. 19 shows the diagnosis of point mutations in the user-assigned genomic region of the DNA sample from ovarian cancer cell line SNU251. A target located at 43047665 on region 2 band 1 of the long arm of chromosome 17 was analyzed in triplicate. The $k_{reaction}$ average value (0.0320) was input into the atlas of MutS affinities to different point mutations, predicting mutations of AC in the target. The insets show the results of control experiments of detecting samples from MCF7 cells.

FIG. 20 shows DNA sequencing results. Compared with the BRCA1 sequence of the cell line MCF7 (negative control without a point mutation), the sequence of SNU251 exhibited a single G>A substitution.

BEST MODE FOR CARRYING OUT THE INVENTION

Unless otherwise defined, all technical and scientific terms used herein have the same meaning as commonly understood by one of ordinary skill in the art to which this invention belongs. In general, the nomenclature used herein is well known and commonly employed in the art.

In one aspect, the present invention is directed to a metal nanobridge structure, specifically a metal nanobridge structure including metal nanoparticles, each of which consists of two metal nanoseeds and a biomolecule anchored between the metal nanoseeds, and a single nanoparticle biosensor platform including the metal nanobridge structure.

In a further aspect, the present invention is directed to a method for constructing a single nanoparticle biosensor platform including forming metal nanoparticles, each of which consists of two metal nanoseeds and a biomolecule anchored between the metal nanoseeds, and creating a metal nanobridge structure using the metal nanoparticles.

In the present invention, the metal is preferably selected from the group consisting of gold (Au), copper (Cu), platinum (Pt), and palladium (Pd), more preferably gold (Au).

In the present invention, the metal nanoseeds are selected from the group consisting of nanospheres, nanorods, nanoprisms, and nanoplates.

In the present invention, the biomolecule is selected from the group consisting of single-stranded DNA, double-stranded DNA, DNA oligomer, RNA oligomer, plasmid DNA, polypeptide, and protein, preferably double-stranded DNA.

In the present invention, the metal nanoseeds preferably have a diameter of 25 nm or less.

In the present invention, the biomolecule preferably has a length of 30 nm or less.

The method of the present invention further includes reducing the metal ions with a reductant on the surface of the metal nanoparticles to grow the metal nanoparticles.

In the present invention, the reductant is hydroxylamine ($NH_2OH$) but is not limited thereto.

In another aspect, the present invention is directed to a biosensor including the single nanoparticle biosensor platform.

The biosensor of the present invention includes a protein, preferably mismatch repair initiation protein (MutS). MutS refers to a protein that recognizes a mismatch in a nucleic acid molecule and can bind to the mismatch site. MutS is also intended to include wild-type proteins having amino acid sequences in which one or more amino acids are substituted, deleted, added, and/or inserted as long as they can recognize mismatches.

The biosensor of the present invention has a higher refractive index (RI) sensitivity than nanorods. The RI sensitivity is defined as the relative change in LSPR peak shift with respect to the refractive index change of a medium surrounding the particles. In the Examples section that follows, the RI sensitivity of the metal nanobridge structure according to the present invention was confirmed to be higher than that of nanorods, which is known to be higher than those of other nanostructures.

The biosensor of the present invention is used to detect mutations, particularly point mutations.

The biosensor of the present invention is used to specify the type of BRCA1 mutations in samples.

In yet another aspect, the present invention is directed to a method for detecting mutations, particularly point mutations using the biosensor.

The method of the present invention is used to identify proteins, preferably mutations, by binding assay of mismatch repair initiation protein (MutS) to mutant nucleic acid molecules.

MODE FOR CARRYING OUT THE INVENTION

Examples

The present invention will be more specifically explained with reference to the following examples. It will be appreciated by those skilled in the art that these examples are merely illustrative and the scope of the present invention is not construed as being limited to the examples. Thus, the true scope of the present invention should be defined by the appended claims and their equivalents.

Example 1: Construction of Single Nanoparticle Sensing Platform and Detection of Point Mutations Using the Single Nanoparticle Sensing Platform

1-1: Materials

Gold nanoseed (AuNS; 5 nm) solution (British BioCell International, Crumlin, UK), wash/storage buffers (10 mM PBS with 0.02% $NaN_3$, 0.01% Tween 20, 0.1% BSA, pH 7.4; Catalog #: WB-100, Ocean NanoTech, San Diego, CA, USA), dithiothreitol (DTT, Promega, Madison, WI, USA) and restriction enzyme StyI (#R648A, Promega, Madison, WI, USA), centrifuges (Microsep® and Nanosep®, Pall Life Sciences, Inc., Ann Arbor, MI, USA), and 2-{2-[2-(2-{2-[2-(1-mercaptoundec-11-yloxy)-ethoxy]-ethoxy}-ethoxy)-ethoxy]-ethoxy}-ethylamine hydrochloride (OEG; Cos Biotech, Daejeon, Korea) were used. MutS protein derived from the thermophilic bacterium *Thermus aquaticus* was supplied by Nippon Gene Co. (Tokyo, Japan) and stored in 20 mM Tris-HCl buffer (pH 7.5) containing 100 mM NaCl, 0.1 mM EDTA, 1 mM DTT, and 50% glycerol at −20° C. G-spin™ Total DNA Extraction Kit (#17046) was supplied by iNtRON Biotechnology (Gyeonggi, Korea). Restriction enzymes MboI (#R0147) and AluI (#R0137) were obtained from NEB (Hitchin, Hertfordshire, UK). Glycogen (#901393) was obtained from Roche (Indianapolis, IN, USA). Poly(ethylene glycol) methyl ether thiol (PEG, Mn=800), hybridization buffer, hybridization wash pack containing single-stranded binding protein, and all other chemical reagents were purchased from Sigma-Aldrich (St. Louis, MO, USA) and used without further purification. All glassware used in the experiments were cleaned in aqua regia solution and rinsed thoroughly with ultrapure water (18.2 mΩ·cm$^{-1}$) before use. All oligonucleotides used were from Integrated DNA Technologies (Coralville, IA, USA). The sequences of the 8 DNA targets containing point mutations am described in Table 1. The corresponding homoduplex (perfectly matched) sequence is as follows: SEQ ID NO: 1. The assigned names and information of single-stranded DNA (ssDNA) are shown in Table 2. The sequences of the DNA targets and probes are shown in Table 2.

TABLE 1

| Mutation name[a] | Genomic location[b] | Allele ID | Nucleotide variant type | Base pairing | Functional consequence | Populations | DNA sequence[c] |
|---|---|---|---|---|---|---|---|
| 4956A>G | GRCh38, 17:43071077.. 43071077 | 50266 | Single substitution A>G | G*-T | Protein changes: S1613G, S1634G, S509G | Worldwide | SEQ ID NO: 2 |
| IVS6-3C>G | GRCh38, 17: 43104264.. 43104264 | 46057 | Single substitution C>G | G*-G | Anomalous splicing leading to premature translation and truncated protein | Worldwide | SEQ ID NO: 3 |
| 5075G>A | GRCh38, 17:43070958.. 43070958 | 50269 | Single substitution G>A | A*-C | Protein changes: M1652I, M1625I, M548I, M1673I | Worldwide | SEQ ID NO: 4 |
| IVS18+1G>T | GRCh38, 17: 43063873.. 43063873 | 70090 | Single substitution G>T | T*-C | Splice donor variant | Worldwide | SEQ ID NO: 5 |
| 5632T>A | GRCh38, 17: 4304575.. 43045757 | 70278 | Single substitution T>A | A*-A | Protein changes: V1838E | Worldwide | SEQ ID NO: 6 |
| 300T>G | GRCh38, 17: 43106487.. 43106487 | 32700 | Single substitution T>G | G*-A | Protein changes: C61G | African American and European | SEQ ID NO: 7 |

TABLE 1-continued

| Mutation name[a] | Genomic location[b] | Allele ID | Nucleotide variant type | Base pairing | Functional consequence | Populations | DNA sequence[c] |
|---|---|---|---|---|---|---|---|
| 5382insC | GRCh38, 17: 43057065.. 43057065 | 32716 | Single duplication | +C | Frameshift variant, non-coding transcript variant | Worldwide | SEQ ID NO: 8 |
| 2594delC | GRCh38, 17: 43093056.. 43093056 | 46028 | Single deletion | -C | Frameshift variant, intron variant, non-coding transcript variant | Originated in Central Europe and most common alterations in Northern Europe | SEQ ID NO: 9 |

[a]BIC (Breast Cancer Information Core): http://research.nhgri.nih.gov/bic/. Nucleotide number according to GenBank U14680.1. http://www.ncbi.nlm.nih.gov/entrez/viewer.fcgi?db=nucleotide&val=555931
[b]http://www.ensembl.org
[c]Twenty five nucleotides before and after the mutation point (the mutant nucleotide is marked in bold).

TABLE 2

| Assigned name | Sequence (5' → 3') | 5'-modification |
|---|---|---|
| SSDNA-1 | SEQ ID NO: 10 | Thiol |
| SSDNA-2 | SEQ ID NO: 11 | Thiol |
| homoDNA | SEQ ID NO: 12 | None |
| New 64-bp probe | SEQ ID NO: 13 | Thiol |

1-2: NP Modeling and Numerical Simulation

Modeling and optical simulations of nanostructures with spherical, rod, and dimeric shapes were performed and NPs were bridged using the software COMSOL. NPs were composed of Au; particle sizes were set as uniform to facilitate comparisons. Final dimensions were determined depending on products synthesized in experiments. Optical simulations were performed in the local dielectric environment where water-glycerol mixtures of varying weight ratios were prepared so that the RI of the surrounding medium ranged from 1.333 to 1.443 (FIG. 1).

1-3: Conjugation of AuNSs with ssDNA

All 5' thiol-modified oligonucleotides were incubated with a 1:100 ratio of OD of oligonucleotide to DTT solution for 15 min and purified two times with ethyl acetate. The disulfide bond of the 5'-thiol was cleaved into an active sulfhydryl form and immediately conjugated with the Au surface. Before conjugation with DNA in solution, AuNSs were coated with bis(p-sulfonatophenyl)phenylphosphine dihydrate dipotassium (BSPP; 100 ml AuNS solution mixed with 100 mg BSPP for 10 h) to improve the tolerance of AuNSs to the highly ionic environment. The AuNS solution was then mixed with NaCl, which resulted in a color change from dark red to light violet. The solution was centrifuged for 30 min at 500× g and the precipitate was resuspended in 1 mL of 0.5 mM BSPP. The solution again changed color from dark red to light violet upon addition of 0.5 mL of methanol; the AuNSs were collected by centrifugation (30 min, 500× g) and dissolved in 1 mL of 0.5×TBE buffer. The concentration of AuNSs was increased to several μM, as measured with an ultraviolet-visible light-near-infrared spectrophotometer (UV-3600; Shimadzu, Kyoto, Japan); 1 OD of 5 nm AuNS is equal to $5.00\times10^{13}$ particles per microliter according to the manufacturer's instructions. The AuNSs were incubated overnight at room temperature with ssDNA-1 in a stoichiometric ratio of 1:1 in 0.5×TBE buffer containing 50 mM NaCl. Thereafter, 60% glycerol was added to the solution to obtain a final mixture of 10% glycerol to prevent AuNS-ssDNA from spreading in the buffers during gel electrophoresis. AuNSs with different numbers of bound ssDNA separated into different bands on a 3% agarose gel in 0.5×TBE buffer at 10 V/cm for 1 h (FIG. 2). The band corresponding to AuNSs conjugated with one strand of ssDNA (AuNS-1ssDNA-1) was incubated in 0.5× TBE buffer for further use. The same incubation and separation procedures were carried out to conjugate AuNSs and ssDNA-2 to obtain AuNS-1ssDNA-2.

1-4: Synthesis-with-Direction of Nanostructures

Gold precursor ($HAuCl_4$, 0.03%) and reductant ($NH_2OH \cdot HCl$, 1 mM) were separately dissolved in water and the pH of each solution was adjusted to 5 or 4 (±0.1) by gradually adding NaOH under a nitrogen environment. The seed for DNA-directed synthesis was produced by hybridization of AuNS-1ssDNA-1 with AuNS-1ssDNA-2 in the form of AuNS-dsDNA-AuNS. To increase hybridization efficiency, equal volumes of the two conjugates in 0.5×TBE were mixed and NaCl was added to increase ionic strength by 100 mM. The mixture was shaken overnight at 37° C. and the AuNS-dsDNA-AuNS was separated by gel electrophoresis with the same procedure as described above (FIG. 2). The gel containing AuNS-dsDNA-AuNS was soaked in 50 mL wash/storage buffer with a final PEG/seed molar ratio of 100:1. The solution was purified and concentrated by centrifugal tubes (molecular weight cut-off 30 K, 3000× g), and thus the seeds were protected by the neutral PEG layer to improve stability and reduce the nonspecific absorption of charged molecules onto the AuNS surface. The seeds were gently stirred with gold precursor for 10 min at a final concentration of 2 nM; 10 μl of the solution was mixed with 17.54 μl reductant, and a color change from colorless to light-red was observed within 1 min. After 15 min, the synthesized NPs were washed by repeated resuspension in water and centrifugation. TEM and HR-TEM images of the NPs were obtained (HD2300; Hitachi) in z-contrast and secondary electron modes at an accelerating voltage of 300 kV. Samples were prepared for TEM using a staining plate (Electron Microscopy Sciences) and 400-mesh copper grids with carbon film(Ted Pella). The lengths and diameters of the nanostructures in the plane of TEM were measured using the software ImageJ. TEM images with scale bars of 20 nm and 50 nm showed nanostructures large enough for precise measurements. Particle yield was calculated as the ratio of Au-bridged NPs to total particles. The undesired particles were easily distinguished as oversized or undersized bridged-nanoparticles and as nanospheres grown from AuNS-ssDNA that were denatured from AuNS-dsDNA-AuNS during the synthetic reaction (Ma,X., et al., Nat Commun 7, 12873, 2016). Fast Fourier transform patterns of HR-TEM images were analyzed with Digital Micrograph software (Gatan, Pleasanton, CA, USA) to confirm the crystalline structure and growth orientation.

1-5: sNPS Platform Settings

The overall configuration of the sNPS system is shown in a of FIG. 3. To construct the detection chamber, microscope glass slides (22×40×0.1 mm; Warner Instruments) were coated with First Contact cleaning polymer (Photonic Cleaning Technologies), which was immediately peeled off after curing for 15 min. The slide was rinsed overnight with aqua regia solution; after rinsing with ultrapure water, the slide was immersed in 5% (v/v) 3-aminopropyltriethoxysilane in absolute ethanol for 15 min followed by sonication in ultrapure water for 5 min. This process was repeated three times. A 3 μl volume of diluted Au-bridged NP solution (OD~0.05) was added as a drop onto the silanized slide, followed by incubation for 1 min at room temperature. The slide was then washed with ultrapure water and ethanol in a biological hood to minimize contaminations with airborne debris, and finally blow-dried with nitrogen gas. The slide was placed in a closed-bath imaging microfluidic chamber (RC-30; Warner Instruments) that was assembled onto a stage controller (Marzhauser Sensotech, Wetzlar, Germany) and connected to a flow device enabling fast turbulent solution mixing and a flow rate control system (PHD 2000; Harvard Apparatus, Holliston, MA, USA). Images and Rayleigh scattering properties of each NP in the chamber were obtained with the sensing system (b of FIG. 3). Images of the field of view of the inverted microscope (Eclipse TE2000-U; Nikon) equipped with a 100 W halogen source (Type 7724, Philips), a dark-field dry condenser (NA=0.80-0.95; Nikon), and 100× objective (CFI Plan Fluor ELWD, NA=0.6; Nikon) were acquired with a color camera (D50; Nikon, Tokyo, Japan), and only individual nanoparticles with interparticle spacing ~5-fold greater than the diameter of shinning dots were analyzed to minimize the effects of interparticle resonance coupling (c of FIG. 3). Images from the chamber were focused on a charge-coupled device (CCD) camera (PIXIS: 400B; Princeton Instruments, Trenton, NJ, USA) at −70° C. with a 100-ms frame integration time. A beam splitter at the output port of the microscope and long-pass filter were placed before the CCD. The platform allowed the determination of Rayleigh light scattering (RLS) properties of each NP in the chamber using an RLS spectrograph (Microspec 2300i; Roper Scientific, Montagne Sud-8, rue du Forez, France) in a darkroom at 18° C. Spectra in a range of 300-900 nm were recorded with acquisition time of 1 s. The spectral data were fitted with the Lorentzian algorithm to eliminate noise, and an accurate $\lambda_{max}$ was determined using Origin2018 software (OriginLab, Northampton, MA, USA). Application of this method to analyze 10 spectra acquired once per minute from the same nanoparticle yielded a fitting-limited peak measurement precision of 0.188 nm (e and f of FIG. 3). The fluctuation in peak positions is attributed to instrumental factors including spectrometer resolution, physical uniformity in chambers, transient variations in temperature, and flow rate of liquid, and analytical factors such as microscope focus control, spectral source correction, exposed pixel selection, and spatial averaging. Besides the fluctuation of 0.188 nm, the total experimental peak uncertainty among random detections of 168 nanoparticles is 0.487 nm, where the 0.299 nm difference resulted from nanoparticle factors of size, shape, and orientation.

1-6: Detection of Point Mutations

After mounting the glass slide in the sNPS platform, the chamber was rinsed by injecting 75% ethanol for 5 min followed by rinsing with wash/storage buffer for 20 min to remove contaminants and unbound Au-NPs. The positions of Au-bridged NPs were recorded after photographing the chamber. One NP was representative to one detection set and its optical properties were determined for each step of molecule binding. The chamber was filled with 100 nM probe DNA (e.g., Probe-GT) for 8 h at room temperature and rinsed with wash/storage buffer for 5 min before introducing target DNA (e.g., 4956A>G) at different concentrations in hybridization buffer. Unbound target was removed by rinsing with the hybridization wash pack before injecting MutS solution at the target concentrations. The binding of MutS with DNA proceeded in binding buffer (pH 7.5; 100 mM NaCl, 1 mM DTT, 0.1 mM EDTA, and 5 mM $MgCl_2$) at a flow rate of 1 μL/min at 18° C. For typical detection, 100 nM target DNA was captured by Probe-T in the chamber and reacted with 20 nM MutS protein for 2 min. Real-time imaging of single NPs with a CCD camera and RLS spectra were recorded and processed using WinSpec software (Roper Scientific). Control experiments under the same detection conditions were conducted to investigate MutS interactions with probes (without target binding) and DNA homoduplex (homoDNA; without a mutation). For the investigations on DNA interactions with nonspecific proteins (without MutS), human serum was introduced after the injection of target DNA with GT mutations. After spectral analysis, the chamber was rinsed with wash/storage buffer at 95° C. for 30 min to remove the proteins. The same serum solution containing 20 nM MutS was injected into the chamber after capturing the same target, and then the spectra were recorded again for further analysis (FIG. 4).

1-7: Preparation and Detection of Samples from Cell Lines

The genomic DNA was extracted using G-spin™ Total DNA Extraction Kit and treated with 200 ng/ml proteinase K and 10 ng/ml RNase A at 55° C. for 30 min before purification and further restriction digestion. The digestion was performed with restriction enzymes MboI, AluI, and StyI to generate 50-60 bp nucleotides. In detail, digestion by MboI and AluI yielded fragments of 100-500 bp. Since there are StyI sites in BRCA1, the fragments were further digested by StyI to the target sample of ~50 bp in length. The specific sites of the enzymes and the computed fragmentation maps can be found in FIGS. 5 and 6. To efficiently collect the DNA, glycogen was added during the ethanol precipitation following by centrifugation for 15 min at 13,000 rpm. The concentration and purity of the DNA were assessed using a Nano-200 Micro-Spectrophotometer DC24V (#AS-11030-00; Allsheng Instruments, Hangzhou, China). The integrity of the DNA was evaluated by gel electrophoresis where 300 ng DNA samples were loaded onto 0.7% agarose gels at 2.5 V·cm−1 at 4° C., stained with 0.5% ethidium bromide, and detected by UV illumination with a Davinch-Gel™ Gel Imaging System (Young Wha Scientific, Seoul, Korea) (FIG. 7); 30 μl of the nucleotides was melted into single-stranded targets at 90° C. for 1 min and injected into the sNPS chamber filled with hybridization buffer at 70° C. for 5 min. Subsequently, the chamber was rinsed by the hybridization wash pack before introducing 20 nM MutS solution in binding buffer at a flow rate of 1 l/min at 18° C. For the diagnosis of the sample from the SNU251 cell line, a new 64-bp probe was designed (see Section 1-1: Materials, supra). Real-time RLS spectra were recorded and the peak positions were analyzed in the wavelength range of 500-650 nm as described above.

1-8: Demonstration of Field of Interest (FOI) of an Individual NP

The plasmonic FOI of an individual nanoparticle is defined as the effective space of plasmonic sensitivity to refractive index changes, where Equation 1 (see Section 1-10: Data analysis, infra) is applicable to calculate the molecular concentration in direct proportion to the amplitude of red shifts in $\lambda_{max}$. The FOI was supposed to be cuboid (a of FIG. 12). The two-dimensional area of the FOI was directly delineated with 8 pixels in CCD images by the WinSpec software of the sensing system (d of FIG. 9), the length and width of which were measured to be 3.36 µm based on the scale calibration (b of FIG. 8). The length and width of this two-dimensional area were set before the spectral monitoring and were maintained for all detections. As shown in c of FIG. 8, the height (h) of the FOI is the sum of the diameter (DNP) and the t of the nanostructure, where t is defined as the threshold thickness of the region that can induce peak red shifts. In detail, LSPR peak shifts exhibit an oscillatory behavior with a periodicity close to the $p=\lambda_{max}/2n$, where n is the refractive index of the coating layer on the surface (d of FIG. 8) (Rindzevicius, T., et al., J Phys Chem C, 111, 11806-11810, 2007). In the first half of the cycle, spectra exhibit red shifts with increasing thickness of less than p/2. Here, the threshold thickness of p/2 is t. Beyond the threshold thickness, the LSPR spectra begin to blue shift and then exhibit a periodic oscillation. Previous studies have demonstrated that the refractive index of the DNA layer ($n_{DNA}$) is 2 and that the proteins and DNA behave similarly with respect to the refractive index change they induce (Thacker, V. V. et al., Nat Commun, 5, 3448, 2014; Liu, G. L. et al., Nature Nanotech, 1, 47-52, 2006; Di Primo, C. et al., Anal Biochem, 368, 148-155, 2007). Therefore, the t of Au-bridged NPs with a $\lambda_{max}$ of 561 nm was calculated to be 70.1 nm. Finally, the volume of the POI ($l \times w \times h = V_{POI}$) was established as 3.36 µm×3.36 µm×0.0844 µm=0.953 $m^3$.

1-9: Estimation of Average Loading Number of Probes (N*) Per NP

The N* was quantitatively predicted based on the modeling of the nanoparticle and DNA footprint (FIG. 10). In detail, N* was calculated by dividing the surface area of a particle by the area of effective footprint of a probe. The footprint is defined as the average area each probe occupies on the nanoparticle surface. Several assumptions were made for the calculation. The nanoparticle was modeled as two perfect spheres bridged by a cylinder, the footprints with the closest distance from each other were modeled as a circular area on the spheres and an ellipse on the cylinder; the contact-points of the two spheres on glass were not considered; and the probes were assumed to be evenly distributed on the particle surface.

The footprint area on the spheres ($S_{sphere}$) is indexed to be 6 $nm^2$ according to the diameter of the sphere. The area of the two spheres ($A_{sphere}$) was calculated by $A_{sphere}=A'_{sphere}-A_{contact}$, where $A'_{sphere}$ is the area of two separated spheres and $A_{contact}$ is the contact area between the spheres and the cylinder; consequently, $A_{sphere}=2\times4\pi(D_{sphere}/2)^2-2\times\pi(D_{bridge}/2)^2=1178$ $nm^2$, and thus the number of probes that can be packed on the spheres was $N^*_{sphere}=A_{sphere}/S_{sphere}=196$.

The footprint area on the outer wall of the cylinder was calculated by the equation: $N^*_{cylinder}=n^*_{short\text{-}axis}\times n^*_{long\text{-}axis}$, where $n^*_{short\text{-}axis}$ is the number of footprints around the circumference and $n^*_{long\text{-}axis}$ is the number down the axis of the cylinder. However, the length of the bridge ($L_{bridge}$=2.39 nm) did not allow more than one row of probe loading along the axis of the cylinder because two rows on a non-curved surface would have a footprint spacing distance (4.72 nm; Hill, H. D. et al., ACS Nano, 3, 418-424, 2009) longer than 2.39 nm. Therefore, $N^*_{cylinder}=n^*_{short\text{-}axis}\times1=\pi D_{bridge}/l_{short\text{-}axis}$, where $D_{bridge}$ is the circumference length and $l_{short\text{-}axis}$ is the short axial length of the footprint given by $l_{short\text{-}axis}=2\times\sqrt{[(3.3618\ \ln(D_{bridge}/2)+0.1616)/\pi]}$. The $N^*_{cylinder}$ was determined to be 11, and finally, $N^*=N^*_{sphere}+N^*_{cylinder}=207$.

Due to the immobilization of the particle on a planar substrate, it was hypothesized that only the surface above the line of "edge of effective loading" can effectively bind with DNA, which covers 59.4% of the total surface area of the particle (FIG. 10). In a saturation condition, all the probes capture targets. Using the established equation of $N_{DNA}=[DNA]V_{FOI}N_A$, the saturation concentration of the target DNA ($[DNA]_{saturation}$) can be predicted by $[DNA]_{saturation}=59.4\%\ N^*/V_{FOI}/N_A=215$ nM.

1-10: Data Analysis

Changes in RI corresponding to each molecular binding step on the NP surface are expressed as LSPR $\lambda_{max}$ shifts ($\Delta\lambda_{max}$):

$$\Delta\lambda_{max} = m(\Delta n)\left[1-\exp(-2d/L_d)\right] \quad (1)$$

where m is the refractive index sensitivity, Δn is the change in refractive index induced by the adsorbate, d is the dielectric thickness and $L_d$ is the electromagnetic field decay length (approximated as an exponential decay; Haes, A. J. et al., J Am Chem Soc, 124, 10596-10604, 2002). The m, $L_d$, and d are variables of the sNPS system for the same nanoparticles and the same lengths of probes and proteins; and therefore, $\Delta\lambda_{max}$ is in direct proportion to Δn, which is proportional to the concentration of the bound analytes (Starov, V. M., Nanoscience: Colloidal and Interfacial Aspects, CRC Press, Boca Raton, FL, 2010). Based on the measurements of $\lambda\lambda_{max}$, the changes in concentrations of the analytes were calculated.

The lowest concentration of MutS protein yielding a reliable $\Delta\lambda_{max}$ was determined as the limit of quantification (LOQ) of the sNPS procedure as follows:

$$LOQ = 10\sigma/S \quad (2)$$

where σ is the standard deviation of the signal and Sis the slope of the calibration curve. The value of a was estimated from the standard deviation of the y intercept of the regression line.

The limit of detection (LOD) of the sNPS system for DNA target was determined as follows:

$$LOD=3.3\sigma/S \tag{3}$$

The signal-to-noise ratio (S/N) was defined as the ratio of the mean (μ) to the standard deviation of $\Delta\lambda_{max}$. An S/N of 5 is the threshold value to distinguish signals at 100% certainty (Bushberg, J. T. et al., Lippincott Williams & Wilkins, Philadelphia, PA, 2012).

$$S/N=\mu/\sigma \tag{4}$$

In the protein-nucleic acid binding reaction, MutS binds DNA, forming the MSDNA complex. Association is a second-order reaction, involving two reactants.

$$MutS+DNA \rightleftharpoons MSDA \tag{5}$$

Conceptually, both the binding and dissociation reactions involve straight binding. At the level of a single DNA strand, MutS association and dissociation are stochastic processes. By simple approximation, all DNA strands on the Au-bridged NP are equally available for binding. The lengths of DNA strands used indicate binding in a 1:1 stoichiometry with MutS; the time course of binding is described by a single exponential process. At the steady state, the rate of binding is equal to the rate of release:

$$k_{binding}[MutS][DNA]=k_{dissociation}[MSDNA] \tag{6}$$

where [MutS] and [DNA] are the free molar concentrations of MutS and DNA, respectively; and $k_{binding}$ and $k_{dissociation}$ are the association and dissociation rate constants, respectively.

Before reaching the steady state, the rate of change in the concentration of the MSDNA complex is equal to the difference between its formation and dissociation rates:

$$d[MSDNA]/dt=k_{binding}[MutS][DNA]-k_{dissociation}[MSDNA] \tag{7}$$

The binding starts at the maximum rate because reactants were not consumed and then slows as reactants are consumed. The extent of the reaction over time can be expressed as follows:

$$[MSDNA] = [MSDNA_{max}]-[MSDNA_{max}]e^{-(k_{binding}[MutS]+k_{dissociation})^{t}}+[MSDNA_{t_n}] \tag{8}$$

The initial concentration of MSDNA ($[MSDNA_m]$) was zero and hence the above equation can be transformed into the following:

$$[MSDNA]=[MSDNA_{max}](1-e^{-k_{reaction}t}) \tag{9}$$

where $k_{reaction}=k_{binding}[MutS]+k_{dissociation}$ is the observed reaction rate constant. The ratio of $k_{dissociation}$ (measures how fast MutS dissociates from DNA) and $k_{binding}$ (measures how fast MutS binds to DNA) yields the equilibrium constant ($K_D$, in nM) of MutS protein, which was used to evaluate the strength of bimolecular interactions and is calculated with the following equation:

$$K_D=\frac{k_{dissociation}}{k_{binding}} \tag{10}$$

Further transformation of the Equations (9) and (10) can get the equation:

$$k_{reaction}=k_{dissociation}\left(\frac{[MutS]}{k_D}+1\right) \tag{11}$$

where $k_{dissociation}$ is independent of concentration and indicates the probability that the complex will spontaneously fall apart in a unit of time (Pollard, T. D. et al., Mol Biol Cell, 24, 1103-1110, 2013).

Based on time courses of the $\lambda_{max}$ change, the time for bindings to reach half of the maximum $\Delta\lambda_{max}$ was evaluated by the half-time of the reaction ($\tau_{1/2}$):

$$\tau_{1/2}=\ln 2/k_{reaction} \tag{12}$$

Example 2: Characterization of the Constructed Single Nanoparticle Sensing Platform and Detection of Point Mutations

2-1: Nanoparticle Design with Numerical Simulations

Since each NP functions as a signal transducer in the sNPS platform, NP structure and shape should be homogeneous and controllable. This excludes irregularly shaped nanocrystals (e.g., branched nanostars), since their formation is empirical rather than scientific based on the principles of synthesis. Furthermore, the controllability of polyhedral nanostructures is limited by the lack of chemicals that can specifically tune targeted crystal facets and thus produce NPs with a relatively high yield. Therefore, nanostructures in the shape of spheres and rods were selected as substrates for sNPS, since both can be synthesized in a uniform and scalable manner. Structures consisting of nanobridges that induce distinct spectral responses and influence the magnitude of plasmonic coupling, polarization direction, signal intensity, and RI sensitivity were also introduced to explore higher RI sensitivity (a of FIG. 11). The sensitivity of metal NPs is a major factor determining the utility of bio/chemical sensors. Optical simulations of single NPs with predesigned structures in which the RI of the surrounding medium was set to change were performed instead of using complex biomarkers to quantify RI sensitivity. Analysis of changes in LSPR wavelength ($\lambda_{max}$) of single Au-NPs induced by different RI solutions was demonstrated to be effective and simple in quantifying RI sensitivity (Truong, P. L., Ma, X. & Sim, S. J. Nanoscale 6, 2307-2315 (2014)). Changes in $\lambda_{max}$ corresponding to each change in RI were observed and expressed as a linear fit (b of FIG. 11) in which the slope of the line represents RI sensitivity of the NPs. Gold nanorods (AuNR) showed higher sensitivity than nanospheres (AuNSph) (Truong, P. L., Ma, X. & Sim, S. J. Nanoscale 6, 2307-2315 (2014)). Nanobridge (Au-bridged NP) structures showed better performance than the nanorod, which was previously thought to be the optimal structure. In particular, the Au-bridged NP showed twofold higher sensitivity than did the AuNR, making it an ultrasensitive candidate material for sNPS fabrication. This is a direct consequence of the high field concentration provided by nanogap and nanobridge structures. Furthermore, plasmonic sensitivity increases proportionally with structural aspect ratio (AR). However, the AR of the Au-bridged NP was set to 2, since larger AR could induce a $\lambda_{max}$ greater than 800 nm after binding of the biological materials outside the wavelength range of the RLS spectrometer.

2-2: Synthesis-by-Design of NPs

The feasibility of "direction-specific" synthesis of gold NPs using double-stranded DNA (dsDNA) was explored by which one dsDNA (~30 nm in length) anchored between two Au nanoseeds (AuNSs; ~5 nm in diameter) served as a direction-specific guide for the crystallization of gold atoms (FIG. 2). Interestingly, altering the surface charge of dsDNA by adjusting the pH also generated nanogaps smaller than 1 nm (c of FIG. 11). At pH 5, dsDNA is slightly negatively charged and electrostatically concentrates $NH_3OH^+$. The reactant pairs, $AuCl_4^-$ and $NH_3OH^+$, are likely to encounter each other, inducing gold crystallization along the DNA to proceed. Crystallization occurred in specific directions from the AuNS-dsDNA boundaries to the mid-point of the dsDNA strand, with nanoscale controllability defined by the length of dsDNA. This method differs fundamentally from conventional approaches involving metallizing DNA or DNA origami, in which either sequential necklaces or continuous bulges are formed with poorly controlled structural precision (>100 nm). Consequently, Au-bridged NPs with a length of 31.15±1.00 nm and a diameter of 14.38±0.58 nm for the two spherical ends and 8.79±0.96 nm for the bridge were formed (Table 3).

TABLE 3

| Au-bridged nanoparticles | Length (nm) Particles | Length (nm) Nanobridges | Diameter (nm) Spherical ends | Diameter (nm) Nanobridges |
|---|---|---|---|---|
| Mean | 31.15 | 2.39 | 14.38 | 8.79 |
| Standard deviation | 1.00 | 0.87 | 0.58 | 0.96 |
| Dimensional deviation[a] | 3.20% | 36.5% | 4.03% | 10.9% |
| p-value[b] | 0.9912 | 0.9786 | 0.9522 | 0.9897 |

[a]Dimensional deviation is the ratio of the standard deviation to the average size.
[b]Nanoparticles were obtained from 8 batches of synthesis and 194 particles in the plane of TEM images were analyzed.

The yield of the desired morphology was 87%, and the nanostructures were in a relatively high monodispersity (FIG. 12). In contrast, at pH 4, dsDNA is positively charged owing to its pI of 4-4.5 (Guo, Z. L. et al., Soft Matter, 12, 6669-6674, 2016). The DNA repelled $NH_3OH^+$ by an electrostatic repulsive force, and therefore, the reaction between $NH_3OH^+$ and $AuC_4^-$ occurred mostly near the AuNS, which further autocatalyzed the crystallization of Au atoms surrounding its surface. The reaction ended with the complete oxidation of Au ions into atoms, leaving a 0.44 nm gap between the two nanospheres (17.01±1.07 nm in diameter).

Crystallization occurred in specific directions from the AuNS-dsDNA boundaries to the mid-point of the dsDNA strand, with nanoscale controllability defined by the length of dsDNA. This method differs fundamentally from conventional approaches involving metallizing DNA or DNA origami, in which either sequential necklaces or continuous bulges are formed with poorly controlled structural precision (>100 nm). The directional effect of DNA in the synthesis of Au-bridged NPs was evaluated by X-ray diffraction and high-resolution transmission electron microscopy (HR-TEM) (d and e of FIG. 11). The AuNSs exhibited peaks of an fcc structure of gold (JCPDS No. 03-0921) at 38° (111) and 44° (200). The peak positions showed clear shifts after DNA-directed crystallization, indicating that the DNA induced significant lattice strain in the Au-bridged nanostructure. The narrower linewidth of the peaks indirectly reflected enlarged particle sizes. Furthermore, HR-TEM images of the nanoscale bridge regime revealed crystal planes with a spacing of 0.208±0.004 nm, corresponding to (200) lattice fringes in the <100> crystallization direction (Ma, X., et al. Nat Commun 7, (2016)). Taken together, DNA realizes direction-specific synthesis of nanoscale bridges and gaps, which can be used for sensitive nanoplasmonic sensing and imaging.

2-3: sNPS with Au-Bridged NPs

Resonant RLS responses of a single Au-bridged NP by sNPS with a white light source were investigated (FIG. 3). Light scattering of individual NPs was observed on a dark-field microscope equipped with a white light source, a dark-field condenser, 100× objective, and a camera. The white light illumination makes it possible to distinguish light scattering from individual NPs with different optical resonances; it also does not induce strong energy and heat that denatures target biomolecules or interfere with molecular interactions. Using a dark field arrangement, light-scattering objects are brightly illuminated against the dark background. Stimulation of LSPR by AuNP strongly improves light scattering enough to be recognized with the naked eye and analyzed by imaging. NPs are sparsely dispersed on the glass substrate of the designed microfluidic reaction chamber. To measure RLS spectrum of a single NP, a highly sensitive charge-coupled device (CCD) and a Rayleigh spectrometer were attached to a microscope. The scattered monochromatic light of a single NP was recorded by the CCD as a function of light scattering intensity versus wavelength in the spectrum. The scattering spectrum was fitted with the Lorentzian algorithm to eliminate noise from the surrounding light.

The light generated LSPR with NPs that sufficiently enhanced light scattering to allow for direct observation of individual NPs; on the other hand, the white light illumination avoided high energy and heat that could denature target biomolecules or block molecular interactions in the microfluidic reaction chamber (a of FIG. 9). The RLS spectrum of a single Au-bridged NP had two surface plasmon peaks (b of FIG. 9): one was related to electron oscillation in the transverse direction, resulting in a relatively weak resonance band around 500 nm (similar to AuNSph), whereas the other was related to electron oscillation in the longitudinal direction around 500 nm (similar to AuNR). The inventors focused on longitudinal surface plasmon peaks since the longitudinal mode is more sensitive to changes in the dielectric constant of the medium than the transverse one (Truong, P. L., Ma, X. & Sim, S. J. Nanoscale 6, 2307-2315 (2014)). The adsorbates of the medium were ssDNA and MutS protein. The probe ssDNA was anchored on Au-bridged NPs by thiol modification and then hybridized with a target ssDNA through hydrogen (H-)bonding and π-π stacking, during which process the $\lambda_{max}$ red shifted from 561.1±0.5 nm to 570.7±0.5 nm (steps 1 and 2; c of FIG. 9). After DNA double helix formation, a red shift around 9 nm was observed at $\lambda_{max}$. Thereafter, MutS protein with a positively charged surface sequence independently contacted the negatively charged DNA backbone. The presence of mismatches in DNA makes the helix complicated and induces specific H-binding of MutS with the conserved Phe-Xaa-Glu motif, resulting in a red shift of up to 24 nm relative to the $\lambda_{max}$ of bare NPs to 585.3±0.5 nm (steps 2 and 3; c of FIG. 9). According to the Mie theory, the LSPR of metallic NPs depends on the shape, size, and RI of the local dielectric environment. Using an individual NP eliminated differences in shape and size; thus, the LSPR $\lambda_{max}$ shifts were attributed to changes in the NP interface upon DNA hybridization and subsequent MutS binding (d of FIG. 9). To verify the specificity of the peak shifts that occurred with the recognition of mutations by MutS, a similar analysis was performed to test the DNA target in human serum without MutS and an analysis was performed to test DNA without mutations (i.e., a perfectly matched target). As expected, few spectral changes were observed in the two analyses (FIG. 4). After introduction of serum solution containing MutS without moving the microfluidic chambers and subsequent heat treatment with wash buffer at 95° C., the detection was repeated. Identically, another significant red shift was observed, confirming that the fabricated sNPS preserved the specificity of MutS for DNA mutations.

2-4: Sensitivity of Sensing

The sensitivity of the sNPS sensing method was investigated according to two parameters: the lowest concentration (LOD) of MutS protein enabling an LSPR $\lambda_{max}$ shift ($\Delta\lambda_{max}$) to be effective within a certain detection time; and the detection time required to reach the LOD. After the MutS solution had arrived at the DNA-modified Au-bridged NPs in the microfluidic chamber, the reaction was allowed to continue for 1 min before obtaining RLS spectra for 10 s. An excess of DNA target was added to ensure complete hybridization with the probes. The effective concentration of MutS protein for the LSPR readout was 6.17 nM, corresponding to a 3.40 nm red shift in $\lambda_{max}$ in the linear range of 10-25 nM MutS (e of FIG. 9). Then, measurements were performed using a blank sample and a series of DNA targets at different concentrations to determine the LOD (f of FIG. 9). The analytical range of 5-150 nM, where a plot of concentrations versus responses went linearly with an $R^2$ of 0.9954, was observed, beyond which the linearity was inconsistent. The S/N was 9.86 while monitoring the 5 nM target. The LOD was calculated as 8.63 nM, which is comparable to that obtained with the label-free QCM method (Su, X. D., Robelek, R., Wu, Y. J., Wang, G. Y. & Knoll, W. Anal. Chem. 76, 489-494 (2004)), and tens of fold lower than the value determined by label-free SPR bulk detection (Gotoh, M., et al. Genet Anal-Biomol E 14, 47-50 (1997)). This high sensitivity was achieved at a flow rate of 1 μL/min, and the total sample volume required for each detection was 30 μL with trace levels of sample. Excess and nonspecific materials were readily washed out of the microfluidic chamber without physical and chemical interference with particle sensing. In contrast, fluorescence sensing methods require large amounts of reagent and many processing steps (e.g., MutS requires long-lasting fluorophore modification at a pre-concentration >3 μM in buffer set to achieve a labeling efficiency of <55%). A gel mobility shift assay requires loading of only a small volume, but samples must be highly concentrated for visualization. The MutS footprint is 24 bp, whereas interactions between protein and DNA are distributed over a large surface area (1250 Å$^2$, ~50 bp). The used 51 bp ssDNA probe ensured clear differentiation between point mutation-induced signal changes and nonspecific binding-induced changes to minimize specific target binding-based signal loss.

2-5: Identification of Single Point Mutations

A design was made to identify eight different point mutations in BRCA1. BRCA) gene mutations include the most important genetic susceptibility of breast cancer, the most frequent cancer of women in the world. Approximately 12% of women will develop breast cancer during their lives, with the highest risk conferred by BRCA1 mutations (59-87%). Except for few common mutations, the spectrum of BRCA1 mutations is heterogeneous in diverse populations. Eight polymorphisms of the BRCA1 gene were selected, including single-nucleotide substitutions (GT, GG, AC, TC, AA, and GA), an insertion (+C), and a deletion (−C) that are most common worldwide. The DNA sequences, mutant names, genomic locations, functional consequences, and target populations are summarized in Table 1. It was speculated that sequence-specific binding of MutS to point mutations alter distinct LSPR signals. In addition, the relative activity of MutS towards different nucleotide variants was examined. Upon injection of the sNPS platform into the sensing chamber, MutS was allowed to bind to DNA-conjugated Au-bridged NPs for 150 s, and the changes in the optical response of a single NP were monitored every 1 s (a of FIG. 13). MutS was loaded on homoduplex (perfectly matched) DNA for ~15 s according to real-time signal responses. This was consistent with a previous report that MutS forms a short-lived clamp and moves along homoduplex DNA by one-dimensional diffusional sliding (Jeong, C., et al. Nat. Struct. Mol. Biol. 18, 379-U174 (2011)). Mismatch identification resulted in a MutS binding time 10-fold longer than that of the homoduplex and induced serial $\Delta\lambda_{max}$. Since this was caused by RI changes upon MutS binding to a DNA-conjugated NP, the time course clearly reflects the distinct activities of MutS in recognizing different point mutations. Different nucleotide variants alter the contact between MutS and DNA. For example, a mismatched thymine forms a hydrogen bond at N3 position with a glutamate of MutS while a mismatched purine forms a hydrogen bond at N7 position. Amino acids, such as phenylalanine, in MutS accumulate nonspecifically around mismatched bases. Such various specific and nonspecific interactions lead to variable reaction constants, which can be determined by kinetic assays of MutS-DNA interactions.

The relative activity of MutS to mutant DNA ($R_{act}$) was defined as the efficiency with which MutS binds to mutant DNA, expressed as $R_{act}=K\times k_{reaction}$, where K is an occupancy constant and $k_{reaction}$ is the rate constant of the protein-DNA interaction. This is a simple approximation of a stochastic binding event in which DNA on the Au-bridged NP is equally available for MutS; therefore, the same detection conditions allow the same K. Accordingly, $R_{act}$ can be evaluated according to $k_{reaction}$. The DNA probe length used (51 bp) implied 1:1 binding stoichiometry with MutS; thus, the time course of binding and disassociation can be described as a single exponential process. By fitting to the exponential equation, the $k_{reaction}$ ($10^{-2}s^{-1}$) values of MutS binding to different DNA targets were 9.95±0.420, 6.15±0.208, 5.80±0.189, 4.92±0.214, 3.82±0.212, 3.60±0.243, 3.25±0.184, and 2.82±0.197 for the point mutations GT, GG, +C, AA, TC, −C, AC, and GA, respectively. By replotting the $k_{reaction}$ values as a function of each target DNA, the order of relative activity of MutS towards the mutations was determined as GT>GG>+C>AA>TC>−C>AC>GA (b of FIG. 3), which is consistent with previous gel mobility shift assay data (DeRocco, V. C., Sass, L. E., Qiu, R. Y., Weninger, K. R. & Erie, D. A. *Biochemistry-Us* 53, 2043-2052(2014)). Point mutations are divided into four types: highly identifiable GT ($k_{reaction}$>0.07), identifiable GG, +C, and AA ($k_{reaction}$=0.05-0.07), highly detectable TC, −C, and AC ($k_{reaction}$=0.03−0.05), and detectable GA ($k_{reaction}$<0.03).

2-6: Reliability of Sensing

The crystal structure and interactions of MutS binding to a GT mismatch have been most clearly demonstrated (Groothuizen, F. S., et al. Elife 4, (2015)). Therefore, the reliability of the sNPS platform was evaluated based on a further analysis of the $k_{reaction}$ of MutS and GT-mutant DNA interaction to form a complex named "MSDNA". The reaction is a second-order reaction, involving two reactants: MutS+DNA⇔MSDNA. The kinetics of MutS binding to and dissociation from DNA can be described as $k_{reaction}=k_{binding}[MutS]+k_{dissociation}$, where $k_{binding}$ and $k_{dissociation}$ are the binding and dissociation rate constants, respectively, and [MutS] represents the free molar concentration of MutS (a of FIG. 14). [MutS] clearly affected reaction kinetics and corresponded to the amplitude of variation in $\Delta\lambda_{max}$. Higher [MutS] induced greater increases in $\lambda_{max}$ prior to equilibrium, ultimately leading to longer shifts at the end of the interaction, which started at the maximum rate since no MutS had been consumed before the reaction slowed in a predictable manner to an equilibrium distribution of MutS. The rate constant $k_{reaction}$ was quantitatively estimated by exponential fitting. Replotting $k_{reaction}$ as a function of [MutS] yielded a linear equation (b of FIG. 14) with $k_{dissociation}$ as the y-intercept and $k_{binding}$ as the slope. The $k_{binding}$ of $2.97\times10^{6}$ $M^{-1}s^{-1}$ was close to previously reported bulk kinetic measurements of 3-$6\times10^{6}$ $M^{-1}s^{-1}$(Qiu, R. Y., et al. *Proc. Natl Acad Sci. USA* 112, 10914-10919 (2015)). Kinetic studies of the ratio between $k_{dissociation}$ and $k_{binding}$ revealed the dissociation equilibrium constant of MutS to DNA, i.e., $K_D$, a fundamental parameter of ligand affinity. The $K_D$ of MutS was found to be 4.46 nM, which was in agreement with reported smFRET and bulk measurements of 2-20 nM (Jeong, C. et al., Nat Struct Mol Biol, 18, 379-385, 2011; Yang, Y. et al., Nucleic Acids Res, 33, 4322-4334, 2005). This is the validation by kinetic studies of the equilibrium constant of MutS on a precise scale around a single NP, and supports the utility of the sNPS assay for diagnostic applications.

2-7: Atlas of MutS Affinities to Point Mutations for Clinical Diagnosis

An atlas of protein binding affinities to DNA with four types of point mutation was further established (FIG. 15): highly identifiable ($k_{reaction}$>0.07), identifiable ($k_{reaction}$=0.05-0.07), highly detectable ($k_{reaction}$=0.03-0.05), and detectable ($k_{reaction}$<0.03). The atlas shows comprehensive information obtained by low-input, high-fidelity sNPS of the relative activity and reaction half-time for each target, mutation type, and diagnostic signal. Specifically, each circle represents a single point mutation, with the diameter and color reflecting the signal response for quantifying the LSPR peak shift and mutation category, respectively. For example, the target DNA with GT mutation generated a peak shift of 14.2 nm, the value of which is affected by and is in proportion to the concentration of targets (100 nM). The mutation category is biologically divided into three types, colored in blue, green, and red, of which the blue one indicates a transition mutation (replacement of a pyrimidine with a pyrimidine or vice versa), the green one indicates a transversion mutation (replacement of a pyrimidine with a purine or vice versa), and the red one indicates a bulging mutation (a base insertion or deletion). The y and x coordinates of the center of each circle represent the relative activity and halftime of the reaction, respectively. The relative activity predicted by $k_{reaction}$ is dependent on the concentration of MutS used in the detections and the $K_D$ of MutS to the target DNA. Therefore, single point mutations can be identified using MutS of the same quality and quantity by this sNPS method. The half-time of the reaction gives knowledge of the time it takes for MutS binding to the individual NPs to reach half of the maximum LSPR shift. Such knowledge can help to explain why, for instance, purine-purine mutations show better repair rates than pyrimidine-pyrimidine mutations in cells, as evidenced by the observation that MutS bound more strongly to the purine-purine mutation (e.g., identifiable GG and AA) than to the pyrimidine-pyrimidine mutation (e.g., highly detectable TC). These results also indicate that repair of AC and GA mutations will be less effective since MutS has lower relative activity towards these than towards TC.

As a proof-of-principle demonstration of clinical applications of the atlas, biological DNA samples were prepared from the human breast cancer cell lines, HCC1937 and MCF7, as an analyte and a control (Elstrodt, F. et al., Cancer Res, 66, 41-45, 2006), respectively, and the presence and type of a potential point mutation among the eight mutations shown in the atlas were detected (FIGS. 5-7). Conspicuously, the glass chip designed for the detection of 5382 insC (Table 1) exhibited a series of peak shifts, while the other chips did not show significant signal variations (FIG. 15). Kinetic studies on the peak shifts in response to the detection time yielded a $k_{reaction}$ of 5.73±0.071 ($10^{-2}s^{-1}$), which was in close proximity to the position of +C in the atlas (FIGS. 15 and 17), demonstrating that BRCA1 of HCC1937 contains a single cytosine duplication. This result was confirmed by DNA sequencing (FIG. 18). Additionally, the circle diameter of the target outputted the information of its concentration; for example, an 8.25 nm diameter indicated a 68.8 nM target according to the circle diameter (12 nm) of the +C in the atlas, which was obtained with a standard concentration of 100 nM.

Finally, this sNPS system was applied to detect potential point mutations in a user-assigned genomic region. A potential BRCA1 point mutation located at 43047665 on region 2 band 1 of the long arm of chromosome 17 was assigned to diagnose an ovarian cancer cell line, SNU251. The chip was fabricated with the same Au-bridged NP but with a new 64-bp probe. Interestingly, continuous shifts of the spectral peaks were observed, validating the effectiveness of the sNPS with the new probe to monitor a specific interval in the gene (FIG. 19). Further, input of the diagnostic results into the atlas indicated that the type of mutation was highly similar to AC point mutation. The $k_{reaction}$ ($10^{-2}s^{-1}$) yielded the similar values (3.20 in the detection versus 3.24 in the atlas), although the flanking sequences of the newly designed probe and the previously used AC probe were different. The small diameter of the purple circle indicated a low concentration of the target upon diagnosis. The prediction of the AC mutation was confirmed to be accurate by DNA sequencing (FIG. 20).

Although the particulars of the present disclosure have been described in detail, it will be obvious to those skilled in the art that such particulars are merely preferred embodiments and are not intended to limit the scope of the present invention. Therefore, the true scope of the present invention is defined by the appended claims and their equivalents.

INDUSTRIAL APPLICABILITY

The single nanoparticle biosensor platform of the present invention can be used to not only detect targets with high sensitivity and reliability, but also to directly identify various mutations, enabling efficient diagnosis of mutations. Therefore, the single nanoparticle biosensor platform of the present invention can be utilized in a wide range of fields, including biomedical diagnostics.

The invention claimed is:

1. A metal nanobridge structure comprising:

a first metal nanoseed;

a second metal nanoseed disposed to face the first metal nanoseed at a predetermined distance; and a nanobridge connecting an end of the first metal nanoseed and an end of the second metal nanoseed, wherein the nanobridge comprises:

a first directionally grown metal crystal structure comprising a first end attached to a surface of the first metal nanoseed and a second end, which is disposed opposite to the first end, attached to a first end of a biomolecule; and a second directionally grown metal crystal structure comprising a first end attached to a surface of the second metal nanoseed and a second end, which is disposed opposite to the first end, attached to a second end of the biomolecule, which is disposed opposite to the first end of the biomolecule, wherein an entire length of the biomolecule is disposed between the first metal nanoseed and the second metal nanoseed, and wherein the first end and the second end of the biomolecule are completely surrounded by the first directionally grown metal crystal structure and the second directionally grown metal crystal structure, respectively, and wherein the biomolecule is double-stranded DNA.

2. The metal nanobridge structure according to claim 1, wherein at least one of the first metal nanoseed and the second metal nanoseed is selected from the group consisting of gold (Au), copper (Cu), platinum (Pt), and palladium (Pd).

3. A method for constructing a biosensor platform, comprising:

(a) disposing a biomolecule between a first metal nanoseed and a second metal nanoseed facing each other at a predetermined distance; and (b) inducing crystallization from the first metal nanoseed and the second metal nanoseed to form a nanobridge thereby connecting an end of the first metal nanoseed and an end of the second metal nanoseed, wherein the nanobridge comprises a first directionally grown metal crystal structure, a biomolecule, and a second directionally grown metal crystal structure, wherein, in step (b), the first directionally grown metal crystal structure is grown from a surface of the first metal nanoseed toward the biomolecule and surrounds a first end of the biomolecule, and a second directionally grown metal crystal structure is grown from a surface of the second metal nanoseed toward the biomolecule and surrounds a second end of the biomolecule, which is disposed opposite to the first end of the biomolecule, and wherein an entire length of the biomolecule is disposed between the first metal nanoseed and the second metal nanoseed, and wherein the first end and the second end of the biomolecule are completely surrounded by the first directionally grown metal crystal structure and the second directionally grown metal crystal structure, respectively, and wherein the biomolecule is double-stranded DNA.

4. The method according to claim 3, wherein at least one of the first metal nanoseed and the second metal nanoseed is selected from the group consisting of gold (Au), copper (Cu), platinum (Pt), and palladium (Pd).

5. The method according to claim 3, wherein, in step (b), metal ions on the surfaces of the first metal nanoseed and the second metal nanoseed are reduced by a reducing agent to grow the first directionally grown metal crystal structure and the second directionally grown metal crystal structure, respectively.

6. The method according to claim 5, wherein the reductant is hydroxylamine ($NH_2OH$).

* * * * *

SEQUENCE LISTING

```
<160> NUMBER OF SEQ ID NOS: 21

<210> SEQ ID NO 1
<211> LENGTH: 51
<212> TYPE: DNA
<213> ORGANISM: Artificial Sequence
<220> FEATURE:
<223> OTHER INFORMATION: homoduplex

<400> SEQUENCE: 1

attgaaagtt gcagaatctg cccagagtcc agctgctgct catactactg a              51


<210> SEQ ID NO 2
<211> LENGTH: 51
<212> TYPE: DNA
<213> ORGANISM: Artificial Sequence
<220> FEATURE:
<223> OTHER INFORMATION: 4956A>G

<400> SEQUENCE: 2

attgaaagtt gcagaatctg cccagggtcc agctgctgct catactactg a              51


<210> SEQ ID NO 3
<211> LENGTH: 51
<212> TYPE: DNA
<213> ORGANISM: Artificial Sequence
<220> FEATURE:
<223> OTHER INFORMATION: IVS6-3C>G

<400> SEQUENCE: 3

acataatgtt ttcccttgta ttttagagat gcaaacagct ataattttgc a              51


<210> SEQ ID NO 4
<211> LENGTH: 51
<212> TYPE: DNA
<213> ORGANISM: Artificial Sequence
<220> FEATURE:
<223> OTHER INFORMATION: 5075G>A

<400> SEQUENCE: 4

aaagggtcaa caaaagaatg tccatagtgg tgtctggcct gaccccagaa g              51


<210> SEQ ID NO 5
<211> LENGTH: 51
<212> TYPE: DNA
<213> ORGANISM: Artificial Sequence
<220> FEATURE:
<223> OTHER INFORMATION: IVS18+1G>T

<400> SEQUENCE: 5

ggaaaatggg tagttagcta tttctttaag tataatacta tttctcccct c              51
```

<210> SEQ ID NO 6
<211> LENGTH: 51
<212> TYPE: DNA
<213> ORGANISM: Artificial Sequence
<220> FEATURE:
<223> OTHER INFORMATION: 5632T>A

<400> SEQUENCE: 6
gcacctgtgg tgacccgaga gtgggagttg gacagtgtag cactctacca g 51

<210> SEQ ID NO 7
<211> LENGTH: 51
<212> TYPE: DNA
<213> ORGANISM: Artificial Sequence
<220> FEATURE:
<223> OTHER INFORMATION: 300T>G

<400> SEQUENCE: 7
caaccagaag aaagggcctt cacagggtcc tttatgtaag aatgatataa c 51

<210> SEQ ID NO 8
<211> LENGTH: 51
<212> TYPE: DNA
<213> ORGANISM: Artificial Sequence
<220> FEATURE:
<223> OTHER INFORMATION: 5382insC

<400> SEQUENCE: 8
caaggtccaa agcgagcaag agaatcccca ggacagaaag gtaaagctcc c 51

<210> SEQ ID NO 9
<211> LENGTH: 51
<212> TYPE: DNA
<213> ORGANISM: Artificial Sequence
<220> FEATURE:
<223> OTHER INFORMATION: 2594delC

<400> SEQUENCE: 9
gttgttccaa agataataga aatgacacag aaggctttaa gtatccattg g 51

<210> SEQ ID NO 10
<211> LENGTH: 100
<212> TYPE: DNA
<213> ORGANISM: Artificial Sequence
<220> FEATURE:
<223> OTHER INFORMATION: ssDNA-1

<400> SEQUENCE: 10
gcagtaacgc tatgtgaccg agaaggattc gcatttgtag tcttgagccc gcacgaaacc 60
tggacacccc taagcaactc cgtaccagat gggaacagca 100

<210> SEQ ID NO 11
<211> LENGTH: 100
<212> TYPE: DNA
<213> ORGANISM: Artificial Sequence
<220> FEATURE:
<223> OTHER INFORMATION: ssDNA-2

<400> SEQUENCE: 11
tgctgttccc atctggtacg gagttgctta ggggtgtcca ggtttcgtgc gggctcaaga 60
ctacaaatgc gaatccttct cggtcacata gcgttactgc 100

<210> SEQ ID NO 12
<211> LENGTH: 51

<212> TYPE: DNA
<213> ORGANISM: Artificial Sequence
<220> FEATURE:
<223> OTHER INFORMATION: homoDNA

<400> SEQUENCE: 12
attgaaagtt gcagaatctg cccagagtcc agctgctgct catactactg a 51

<210> SEQ ID NO 13
<211> LENGTH: 64
<212> TYPE: DNA
<213> ORGANISM: Artificial Sequence
<220> FEATURE:
<223> OTHER INFORMATION: New 64-bp probe

<400> SEQUENCE: 13
gaagccattg tcctctgtcc aggcatctgg ctgcacaacc acaattgggt ggacaccctg 60
gatc 64

<210> SEQ ID NO 14
<211> LENGTH: 51
<212> TYPE: DNA
<213> ORGANISM: Artificial Sequence
<220> FEATURE:
<223> OTHER INFORMATION: Forward sequence of MCF7

<400> SEQUENCE: 14
ccaccaaggt ccaaagcgag caagagaatc ccaggacaga aaggtaaagc t 51

<210> SEQ ID NO 15
<211> LENGTH: 51
<212> TYPE: DNA
<213> ORGANISM: Artificial Sequence
<220> FEATURE:
<223> OTHER INFORMATION: Reverse sequence of MCF7

<400> SEQUENCE: 15
ggtggttcca ggtttcgctc gttctcttag ggtcctgtct ttccatttcg a 51

<210> SEQ ID NO 16
<211> LENGTH: 52
<212> TYPE: DNA
<213> ORGANISM: Artificial Sequence
<220> FEATURE:
<223> OTHER INFORMATION: Forward sequence of MCF1937

<400> SEQUENCE: 16
ccaccaaggt ccaaagcgag caagagaatc cccaggacag aaaggtaaag ct 52

<210> SEQ ID NO 17
<211> LENGTH: 52
<212> TYPE: DNA
<213> ORGANISM: Artificial Sequence
<220> FEATURE:
<223> OTHER INFORMATION: Reverse sequence of MCF1937

<400> SEQUENCE: 17
ggtggttcca ggtttcgctc gttctcttag gggtcctgtc tttccatttc ga 52

<210> SEQ ID NO 18
<211> LENGTH: 74
<212> TYPE: DNA
<213> ORGANISM: Artificial Sequence
<220> FEATURE:
<223> OTHER INFORMATION: Forward sequence of MCF7

-continued

<400> SEQUENCE: 18

```
tggggatcca gggtgtccac ccaattgtgg ttgtgcagcc agatgcctgg acagaggaca     60

atggcttcca tggt                                                       74
```

<210> SEQ ID NO 19
<211> LENGTH: 74
<212> TYPE: DNA
<213> ORGANISM: Artificial Sequence
<220> FEATURE:
<223> OTHER INFORMATION: Reverse sequence of MCF7

<400> SEQUENCE: 19

```
acccctaggt cccacaggtg ggttaacacc aacacgtcgg tctacggacc tgtctcctgt     60

taccgaaggt acca                                                       74
```

<210> SEQ ID NO 20
<211> LENGTH: 74
<212> TYPE: DNA
<213> ORGANISM: Artificial Sequence
<220> FEATURE:
<223> OTHER INFORMATION: Forward sequence of SUN251

<400> SEQUENCE: 20

```
tggggatcca gggtgtccac ccaattgtgg ttgtgcagcc agatgcctga acagaggaca     60

atggcttcca tggt                                                       74
```

<210> SEQ ID NO 21
<211> LENGTH: 74
<212> TYPE: DNA
<213> ORGANISM: Artificial Sequence
<220> FEATURE:
<223> OTHER INFORMATION: Reverse sequence of SUN251

<400> SEQUENCE: 21

```
acccctaggt cccacaggtg ggttaacacc aacacgtcgg tctacggact tgtctcctgt     60

taccgaaggt acca                                                       74
```